US012575755B2

(12) United States Patent
Sarkar et al.

(10) Patent No.: US 12,575,755 B2
(45) Date of Patent: Mar. 17, 2026

(54) DETERMINING HEALTH CONDITION STATUSES USING SUBCUTANEOUS IMPEDANCE MEASUREMENTS

(71) Applicant: Medtronic, Inc., Minneapolis, MN (US)

(72) Inventors: Shantanu Sarkar, Roseville, MN (US); Todd M. Zielinski, Ham Lake, MN (US); Brian B. Lee, Golden Valley, MN (US); Val D. Eisele, III, Little Canada, MN (US); Eduardo N. Warman, Maple Grove, MN (US); Matthew T Reinke, Roseville, MN (US); Ekaterina M. Ippolito, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 113 days.

(21) Appl. No.: 17/021,564

(22) Filed: Sep. 15, 2020

(65) Prior Publication Data
US 2021/0093220 A1 Apr. 1, 2021

Related U.S. Application Data

(60) Provisional application No. 62/906,979, filed on Sep. 27, 2019.

(51) Int. Cl.
*A61B 5/053* (2021.01)
*A61B 5/00* (2006.01)
(Continued)

(52) U.S. Cl.
CPC .......... *A61B 5/0538* (2013.01); *A61B 5/0031* (2013.01); *A61B 5/029* (2013.01);
(Continued)

(58) Field of Classification Search
CPC .............................. A61B 5/0205; A61B 5/053
See application file for complete search history.

(56) References Cited

U.S. PATENT DOCUMENTS 3,724,455 A 4/1973 Unger
3,872,252 A 3/1975 Malchman et al.
(Continued)

FOREIGN PATENT DOCUMENTS

CN 1353619 A 6/2002
CN 102946800 A 2/2013
(Continued)

OTHER PUBLICATIONS

International Search Report and Written Opinion of International Application No. PCT/US2020/052080, mailed Mar. 1, 2021, 10 pp.
(Continued)

*Primary Examiner* — Michael J D'Abreu
(74) *Attorney, Agent, or Firm* — Shumaker & Sieffert, P.A.

(57) ABSTRACT

Techniques for obtaining impedance data to provide an early warning for heart failure decompensation are described. An example device may be configured to measure subcutaneous impedance values, and increment an impedance score. In some examples, the device may use an adaptive threshold and fluid index in incrementing the impedance score. In some examples, the impedance score is compared to a threshold to determine a heart failure status of a patient. In some examples, may cause resets in fluid index values and/or determine positions or orientations of the device when determining the impedance score.

27 Claims, 10 Drawing Sheets

(51) Int. Cl.

| | |
|---|---|
| *A61B 5/029* | (2006.01) |
| *A61B 5/0538* | (2021.01) |
| *A61B 5/06* | (2006.01) |
| *A61B 5/318* | (2021.01) |

(52) U.S. Cl.
CPC .............. *A61B 5/067* (2013.01); *A61B 5/068* (2013.01); *A61B 5/318* (2021.01); *A61B 5/6869* (2013.01); *A61B 2562/0219* (2013.01)

(56) References Cited

U.S. PATENT DOCUMENTS

| | | | |
|---|---|---|---|
| 4,108,166 A | 8/1978 | Schmid | |
| 4,374,382 A | 2/1983 | Markowitz | |
| 4,823,797 A | 4/1989 | Heinze et al. | |
| 5,107,833 A | 4/1992 | Barsness | |
| 5,117,824 A | 6/1992 | Keimel et al. | |
| 5,168,871 A | 12/1992 | Grevious | |
| 5,271,395 A | 12/1993 | Wahlstrand et al. | |
| 5,292,343 A | 3/1994 | Blanchette et al. | |
| 5,314,450 A | 5/1994 | Thompson | |
| 5,324,315 A | 6/1994 | Grevious | |
| 5,354,319 A | 10/1994 | Wybory et al. | |
| 5,383,909 A | 1/1995 | Keimel | |
| 5,545,186 A | 8/1996 | Olson et al. | |
| 5,755,736 A | 5/1998 | Gillberg et al. | |
| 5,836,975 A | 11/1998 | DeGroot | |
| 5,876,353 A * | 3/1999 | Riff | A61B 5/0537 |
| | | | 607/9 |
| 5,957,861 A | 9/1999 | Combs et al. | |
| 6,045,513 A | 4/2000 | Stone et al. | |
| 6,102,874 A | 8/2000 | Stone et al. | |
| 6,104,949 A | 8/2000 | Crick et al. | |
| 6,148,233 A | 11/2000 | Owen et al. | |
| 6,154,674 A | 11/2000 | Meier | |
| 6,221,011 B1 | 4/2001 | Bardy | |
| 6,263,243 B1 | 7/2001 | Lang | |
| 6,277,072 B1 | 8/2001 | Bardy | |
| 6,280,380 B1 | 8/2001 | Bardy | |
| 6,280,409 B1 | 8/2001 | Stone et al. | |
| 6,336,903 B1 | 1/2002 | Bardy | |
| 6,405,085 B1 | 6/2002 | Graupner et al. | |
| 6,449,509 B1 | 9/2002 | Park et al. | |
| 6,459,929 B1 | 10/2002 | Hopper et al. | |
| 6,463,326 B1 | 10/2002 | Hartley et al. | |
| 6,473,640 B1 | 10/2002 | Erlebacher | |
| 6,480,733 B1 | 11/2002 | Turcott | |
| 6,512,949 B1 | 1/2003 | Combs et al. | |
| 6,572,557 B2 | 6/2003 | Tchou et al. | |
| 6,595,927 B2 | 7/2003 | Pitts-Crick et al. | |
| 6,599,250 B2 | 7/2003 | Webb et al. | |
| 6,671,549 B2 | 12/2003 | Van Dam et al. | |
| 6,709,390 B1 | 3/2004 | Marie Pop | |
| 6,821,249 B2 | 11/2004 | Casscells, III et al. | |
| 6,866,629 B2 | 3/2005 | Bardy | |
| 6,895,275 B2 | 5/2005 | Markowitz et al. | |
| 6,907,288 B2 | 6/2005 | Daum | |
| 6,931,272 B2 | 8/2005 | Burnes | |
| 6,945,934 B2 | 9/2005 | Bardy | |
| 6,960,167 B2 | 11/2005 | Bardy | |
| 7,020,521 B1 | 3/2006 | Brewer et al. | |
| 7,127,290 B2 | 10/2006 | Girouard et al. | |
| 7,177,681 B2 | 2/2007 | Zhu | |
| 7,184,821 B2 | 2/2007 | Belalcazar et al. | |
| 7,248,916 B2 | 7/2007 | Bardy | |
| 7,272,442 B2 | 9/2007 | Freeberg | |
| 7,308,309 B1 | 12/2007 | Koh | |
| 7,310,551 B1 | 12/2007 | Koh et al. | |
| 7,313,434 B2 | 12/2007 | Belalcazar et al. | |
| 7,340,296 B2 | 3/2008 | Stahmann et al. | |
| 7,387,610 B2 | 6/2008 | Stahmann et al. | |
| 7,389,143 B2 | 6/2008 | Hopper et al. | |
| 7,774,055 B1 | 8/2010 | Min | |
| 7,986,994 B2 | 7/2011 | Stadler et al. | |
| 8,052,611 B2 | 11/2011 | Wariar et al. | |
| 8,255,046 B2 | 8/2012 | Sarkar et al. | |
| 8,708,924 B2 | 4/2014 | Wariar et al. | |
| 8,744,565 B2 | 6/2014 | Zielinski et al. | |
| 8,750,998 B1 | 6/2014 | Ghosh et al. | |
| 8,777,850 B2 | 7/2014 | Cho et al. | |
| 8,938,286 B2 | 1/2015 | Dumont et al. | |
| 9,138,151 B2 | 9/2015 | Wariar et al. | |
| 9,147,041 B2 | 9/2015 | Amarasingham et al. | |
| 9,173,615 B2 | 11/2015 | Katra et al. | |
| 9,345,414 B1 | 5/2016 | Bardy et al. | |
| 9,615,744 B2 | 4/2017 | Denison et al. | |
| 10,368,774 B2 | 8/2019 | Sharma et al. | |
| 10,702,213 B2 | 7/2020 | Sharma et al. | |
| 11,568,993 B2 | 1/2023 | Zaphrir et al. | |
| 2001/0011153 A1 | 8/2001 | Bardy | |
| 2001/0021801 A1 | 9/2001 | Bardy | |
| 2001/0039504 A1 | 11/2001 | Lindberg et al. | |
| 2002/0026104 A1 | 2/2002 | Bardy | |
| 2002/0035380 A1* | 3/2002 | Rissmann | A61N 1/3956 |
| | | | 607/4 |
| 2003/0028221 A1 | 2/2003 | Zhu et al. | |
| 2003/0055461 A1 | 3/2003 | Girouard et al. | |
| 2003/0125611 A1 | 7/2003 | Bardy | |
| 2003/0149367 A1 | 8/2003 | Kroll et al. | |
| 2003/0216654 A1 | 11/2003 | Xu et al. | |
| 2003/0220580 A1 | 11/2003 | Alt | |
| 2004/0102712 A1 | 5/2004 | Belalcazar et al. | |
| 2004/0122484 A1 | 6/2004 | Hatlestad et al. | |
| 2004/0172080 A1* | 9/2004 | Stadler | A61B 5/4875 |
| | | | 607/17 |
| 2005/0124908 A1 | 6/2005 | Belalcazar et al. | |
| 2006/0010090 A1 | 1/2006 | Brockway et al. | |
| 2006/0020295 A1 | 1/2006 | Brockway et al. | |
| 2006/0293609 A1 | 12/2006 | Stahmann et al. | |
| 2007/0142732 A1 | 6/2007 | Brockway et al. | |
| 2007/0156061 A1* | 7/2007 | Hess | A61B 5/0538 |
| | | | 600/595 |
| 2007/0239043 A1 | 10/2007 | Patel et al. | |
| 2008/0004664 A1 | 1/2008 | Hopper et al. | |
| 2008/0024293 A1 | 1/2008 | Stylos | |
| 2008/0027349 A1 | 1/2008 | Stylos | |
| 2008/0161657 A1 | 7/2008 | Kessels et al. | |
| 2008/0228090 A1 | 9/2008 | Wariar et al. | |
| 2009/0030292 A1 | 1/2009 | Bartnik et al. | |
| 2009/0281399 A1 | 11/2009 | Keel et al. | |
| 2010/0030086 A1 | 2/2010 | Zielinski et al. | |
| 2010/0030292 A1 | 2/2010 | Sarkar et al. | |
| 2010/0030293 A1 | 2/2010 | Sarkar et al. | |
| 2010/0113888 A1 | 5/2010 | Cho et al. | |
| 2010/0114241 A1 | 5/2010 | Donofrio et al. | |
| 2010/0152802 A1 | 6/2010 | Min | |
| 2010/0198097 A1 | 8/2010 | Sowelam | |
| 2011/0009760 A1 | 1/2011 | Zhang et al. | |
| 2012/0109243 A1 | 5/2012 | Hettrick et al. | |
| 2012/0157856 A1 | 6/2012 | An et al. | |
| 2012/0221069 A1* | 8/2012 | Rosenberg | A61N 1/36592 |
| | | | 607/18 |
| 2012/0253207 A1 | 10/2012 | Sarkar et al. | |
| 2013/0116578 A1 | 5/2013 | An et al. | |
| 2013/0116583 A1* | 5/2013 | Min | A61B 5/283 |
| | | | 600/509 |
| 2014/0330172 A1 | 11/2014 | Jovanov et al. | |
| 2015/0157273 A1* | 6/2015 | An | A61B 5/7275 |
| | | | 600/595 |
| 2015/0327776 A1 | 11/2015 | Zhang et al. | |
| 2016/0038093 A1 | 2/2016 | Sharma et al. | |
| 2016/0157769 A1* | 6/2016 | Min | A61B 5/0536 |
| | | | 600/547 |
| 2016/0206250 A1 | 7/2016 | Sharma et al. | |
| 2016/0361026 A1 | 12/2016 | Sarkar et al. | |
| 2017/0181677 A1 | 6/2017 | Varsavsky et al. | |
| 2017/0238812 A1 | 8/2017 | Atlas et al. | |
| 2017/0245794 A1 | 8/2017 | Sharma et al. | |
| 2017/0265782 A1 | 9/2017 | Vollmer | |
| 2017/0354365 A1 | 12/2017 | Zhou | |
| 2017/0360320 A1 | 12/2017 | Sarkar et al. | |
| 2018/0021570 A1 | 1/2018 | An et al. | |
| 2018/0035898 A1 | 2/2018 | Gunderson | |
| 2019/0006985 A1 | 1/2019 | Twisselman | |

(56)                    References Cited

U.S. PATENT DOCUMENTS

| | | | |
|---|---|---|---|
| 2019/0069851 A1 | 3/2019 | Sharma et al. | |
| 2019/0083030 A1 | 3/2019 | Thakur et al. | |
| 2019/0125273 A1 | 5/2019 | Sharma et al. | |
| 2019/0183339 A1 | 6/2019 | Shah et al. | |
| 2019/0336077 A1 | 11/2019 | Kuhn et al. | |
| 2020/0129099 A1* | 4/2020 | Mi ...................... | A61B 5/0006 |
| 2020/0337563 A1 | 10/2020 | Andersen | |
| 2020/0383597 A1 | 12/2020 | Rajagopal et al. | |
| 2020/0383647 A1 | 12/2020 | Freeman et al. | |

FOREIGN PATENT DOCUMENTS

| | | |
|---|---|---|
| CN | 105792741 A | 7/2016 |
| CN | 107921266 A | 4/2018 |
| CN | 108348745 A | 7/2018 |
| DE | 10148440 A1 | 4/2003 |
| EP | 1997427 A1 | 3/2008 |
| WO | 98033554 A1 | 8/1998 |
| WO | 200064336 A1 | 11/2000 |
| WO | 2001032260 A1 | 5/2001 |
| WO | 2004045406 A1 | 6/2004 |
| WO | 2005110051 A2 | 11/2005 |
| WO | 2006/070124 A1 | 7/2006 |
| WO | 2006081432 A1 | 8/2006 |
| WO | 2007079354 A2 | 7/2007 |
| WO | 2009063446 | 5/2009 |
| WO | 2010014066 A | 2/2010 |
| WO | 2010042855 A1 | 4/2010 |
| WO | 2011126823 A1 | 10/2011 |
| WO | 2013022760 A1 | 2/2013 |
| WO | 2013082126 A1 | 6/2013 |
| WO | 2015175207 A1 | 11/2015 |
| WO | 20150175207 A1 | 11/2015 |

OTHER PUBLICATIONS

Gholamhosseini et al, "Smartphone-Based Blood Pressure Monitoring for Falls Risk Assessment: Techniques and Technologies," Human Monitoring, Smart Health and Assisted Living, May 31, 2017, pp. 203-215.
International Search Report and Written Opinion of International Application No. PCT/US2020/052081, mailed Nov. 30, 2020, 9 pp.
Murphy, "A Brief Introduction to Graphical Models and Bayesian Networks", 1998, 27 pp. (Applicant points out, in accordance with MPEP 609.04(a), that the year of publication, 1998, is sufficiently earlier than the effective U.S. filing date, so that the particular month of publication is not an issue.). Retrieved from the Internet from URL: https://www.cs.ubc.ca/-murphyk/Bayes/bnintro.htrnl.
Baer, et al. "Electronic Home Monitoring of Congestive Heart Failure Patients: Design and Feasibility", Congestive Heart Failure, 5:105-113, May-Jun. 1999.
Cowie et al., "Development and validation of an integrated diagnostic algorithm derived from parameters monitored in implantable devices for identifying patients at risk for heart failure hospitalization in an ambulatory setting," European Heart Journal, vol. 34, Mar. 19, 2013, pp. 2472-2480.
U.S. Appl. No. 16/450,250, filed Jun. 24, 2019, by Sarkar et al.
Yu et al., "Intrathoracic Impedance Monitoring in Patients With Heart Failure," Circulation, vol. 112, No. 6, Aug. 9, 2005, pp. 841-848.
Adamson et al., "Wireless Pulmonary Artery Pressure Monitoring Guides Management to Reduce Decompensation in Heart Failure With Preserved Ejection Fraction," Circ Hear Fail, Nov. 2014, pp. 935-944.
U.S. Appl. No. 17/021,489, filed Sep. 15, 2020, by Sarkar et al.
U.S. Appl. No. 17/021,521, filed Sep. 15, 2020, by Sarkar et al.
Adamson et al, "Continuous Autonomic Assessment in Patients with Symptomatic Heart Failure . . . " Circulation Journal of American Heart Association, pp. 2389-2394. 110: 16, Lippincott Williams & Wilkins, Baltimore MD, Jun. 30, 2004.

Athanasiou M. et al., "A Bayesian Network Model for the Diagnosis of the Caring Procedure for Wheelchair Users With Spinal Injury" Computer Methods and Programs in Biomedicine, Elsevier, Amsterdam, NL vol. 95, No. 2, Aug. 1, 2009, pp. 844-854.
Berman et al. "Transthoracic Electrical Impedance as a Guide to Intravascular Overload", Archives Surgery, 102, pp. 61-64 Jan. 1971.
Gholamhosseini et al., "Smartphone-based blood pressure monitoring for falls risk assessment: techniques and technologies," Human Monitoring, Smart Health and Assisted Living: Techniques and Technologies, May 31, 2017, pp. 203-215.
Lusignan, et al. "Compliance and Effectiveness of 1 Year's Home Telemonitoring, The Report of a Pilot Study . . . " European Journal of Heart Failure, 3:723-730, Dec. 2001.
Office Action from U.S. Appl. No. 17/021,489 dated Sep. 28, 2022, 22 pp.
Wuerz et al., "Effects of Prehospital Medications on Mortality and Length of Stay in Congestive Heart Failure", Annals of Emergency Medicine 21:6 pp. 669-674, Jun. 1992.
Advisory Action from U.S. Appl. No. 17/021,489 dated Mar. 7, 2023, 3 pp.
Response to Final Office Action dated Jan. 13, 2022 from U.S. Appl. No. 17/021,489, filed Feb. 27, 2023, 17 pp.
Final Office Action from U.S. Appl. No. 17/021,489 dated Jan. 13, 2023, 22 pp.
Response to Office Action dated Sep. 28, 2022 from U.S. Appl. No. 17/021,489, filed Dec. 21, 2022, 20 pp.
Response to Office Action dated May 9, 2023 from U.S. Appl. No. 17/021,489, filed Aug. 9, 2023, 15 pp.
Office Action from U.S. Appl. No. 17/021,489 dated May 9, 2023, 24 pp.
Response to Office Action dated Feb. 7, 2024 from U.S. Appl. No. 17/021,489, filed Apr. 11, 2024, 12 pp.
Office Action from U.S. Appl. No. 17/021,489 dated May 17, 2024, 26 pp.
Advisory Action from U.S. Appl. No. 17/021,489 dated Nov. 22, 2023, 3 pp.
Final Office Action from U.S. Appl. No. 17/021,489 dated Sep. 15, 2023, 24 pp.
Prutchi et al., "Design and Development of Medical Electronic Instrumentation: A Practical Perspective of the Design, Construction, and Test of Medical Devices", John Wiley & Sons, Jan. 28, 2005, pp. 400-401.
Response to Final Office Action dated Sep. 15, 2023 from U.S. Appl. No. 17/021,489, filed Nov. 13, 2023, 12 pp.
Office Action from U.S. Appl. No. 17/021,489 dated Feb. 7, 2024, 26 pp.
Response to Final Office Action dated Sep. 15, 2023 from U.S. Appl. No. 17/021,489, filed Dec. 15, 2023, 21 pp.
Advisory Action from U.S. Appl. No. 17/021,489 dated Nov. 6, 2024, 3 pp.
Office Action from U.S. Appl. No. 17/021,489 dated Feb. 12, 2025, 30 pp.
Response to Final Office Action dated Aug. 23, 2024 from U.S. Appl. No. 17/021,489, filed Nov. 22, 2024, 25 pp.
Response to Final Office Action dated Aug. 23, 2024 from U.S. Appl. No. 17/021,489, filed Oct. 23, 2024, 20 pp.
Final Office Action from U.S. Appl. No. 17/021,489 dated Jun. 6, 2025, 11 pp.
First Office Action and Search Report, and translation thereof, from counterpart Chinese Application No. 202080067435.1 dated Apr. 27, 2025, 12 pp.
Response to Office Action dated Feb. 12, 2025 from U.S. Appl. No. 17/021,489, filed May 12, 2025, 60 pp.
Final Office Action from U.S. Appl. No. 17/021,489 dated Aug. 23, 2024, 28 pp.
Response to Office Action dated May 17, 2024 from U.S. Appl. No. 17/021,489, filed Aug. 8, 2024, 10 pp.
Appeal Brief from U.S. Appl. No. 17/021,489, filed Nov. 7, 2025, 39 pp.

(56)          References Cited

OTHER PUBLICATIONS

Notice of Allowance from U.S. Appl. No. 17/021,489 dated Jan. 14, 2026, 8 pp.

* cited by examiner

2

12

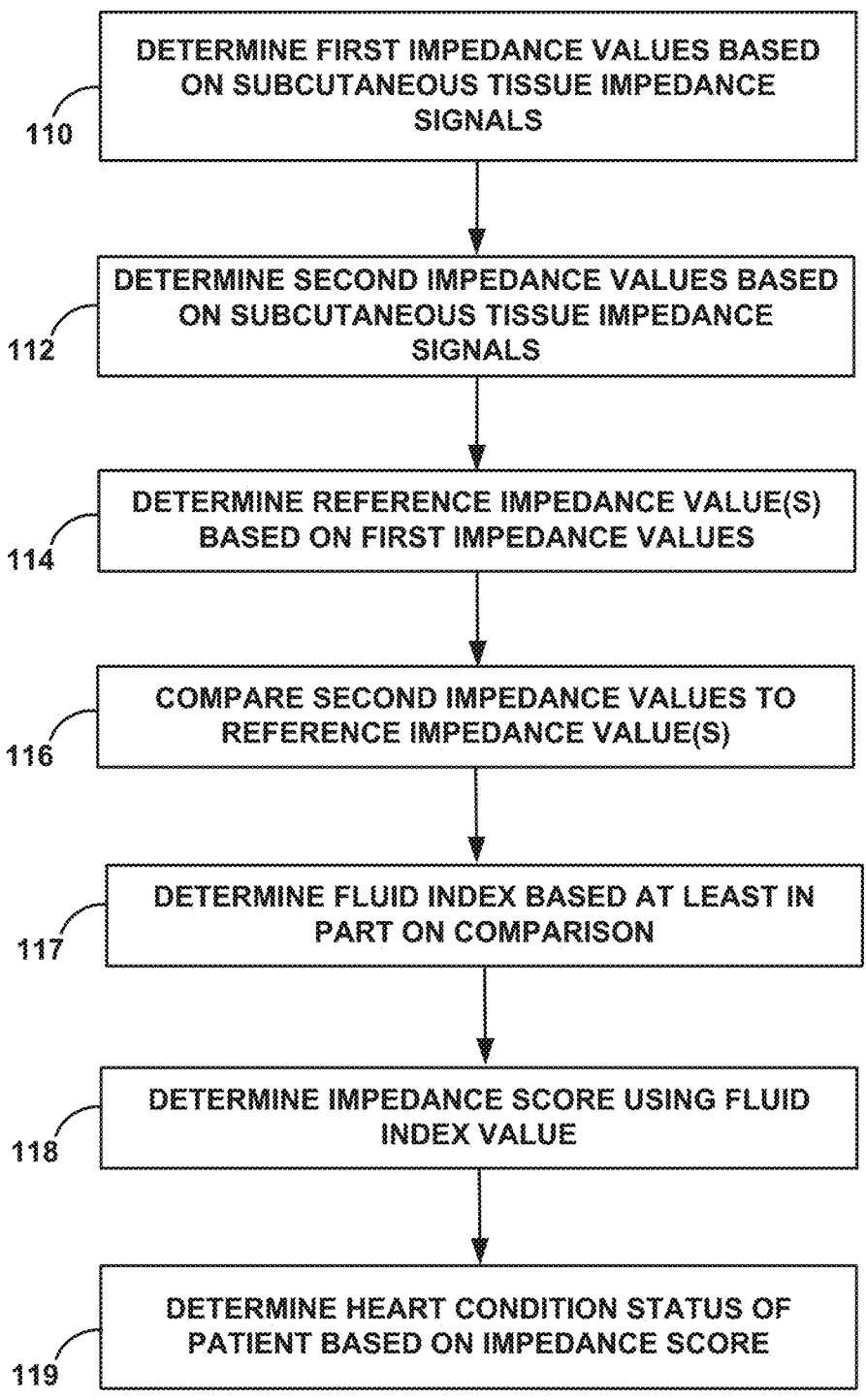

110 — DETERMINE FIRST IMPEDANCE VALUES BASED ON SUBCUTANEOUS TISSUE IMPEDANCE SIGNALS

112 — DETERMINE SECOND IMPEDANCE VALUES BASED ON SUBCUTANEOUS TISSUE IMPEDANCE SIGNALS

114 — DETERMINE REFERENCE IMPEDANCE VALUE(S) BASED ON FIRST IMPEDANCE VALUES

116 — COMPARE SECOND IMPEDANCE VALUES TO REFERENCE IMPEDANCE VALUE(S)

117 — DETERMINE FLUID INDEX BASED AT LEAST IN PART ON COMPARISON

118 — DETERMINE IMPEDANCE SCORE USING FLUID INDEX VALUE

119 — DETERMINE HEART CONDITION STATUS OF PATIENT BASED ON IMPEDANCE SCORE

FIG. 6

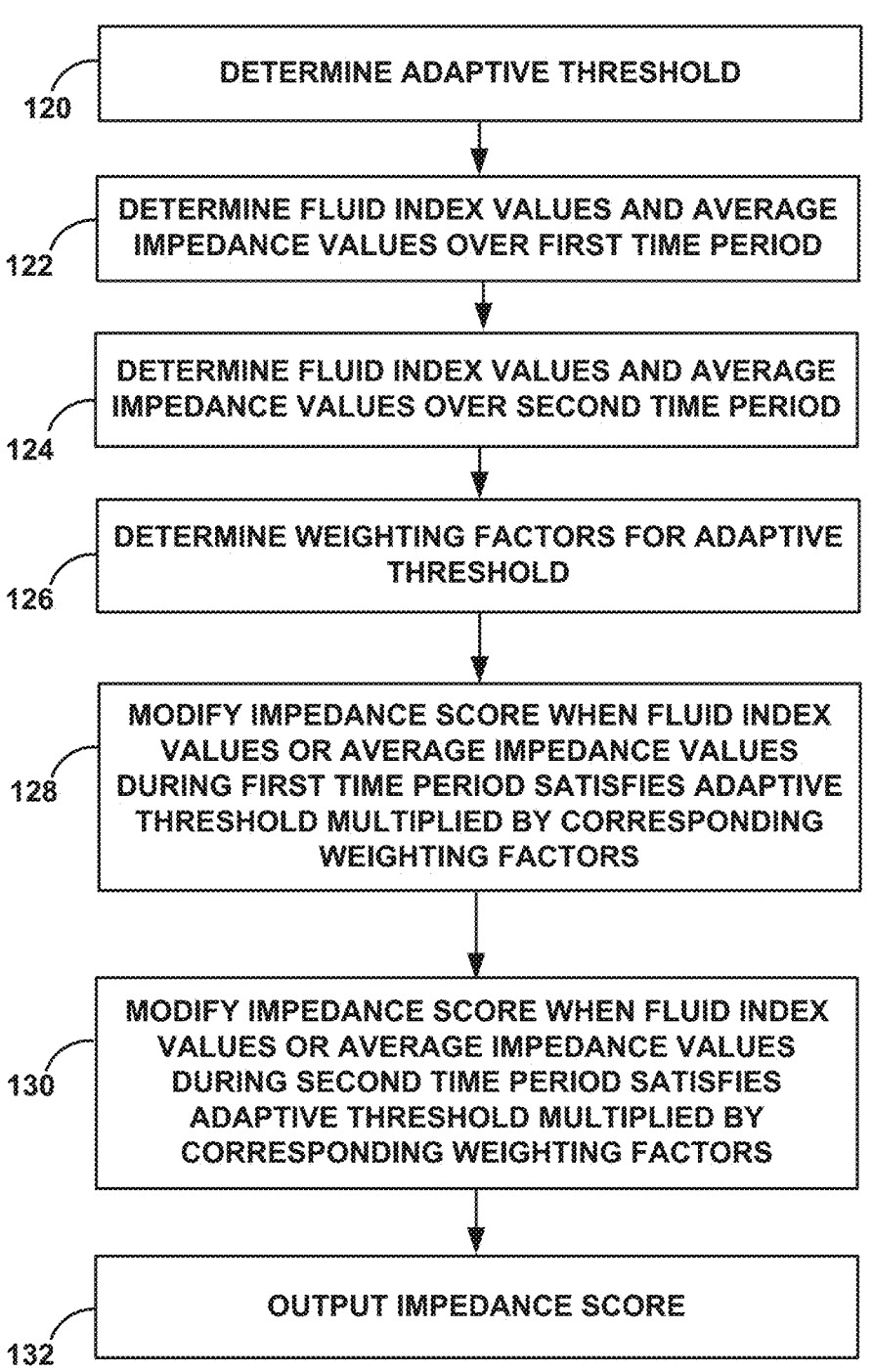

120   DETERMINE ADAPTIVE THRESHOLD

122   DETERMINE FLUID INDEX VALUES AND AVERAGE IMPEDANCE VALUES OVER FIRST TIME PERIOD

124   DETERMINE FLUID INDEX VALUES AND AVERAGE IMPEDANCE VALUES OVER SECOND TIME PERIOD

126   DETERMINE WEIGHTING FACTORS FOR ADAPTIVE THRESHOLD

128   MODIFY IMPEDANCE SCORE WHEN FLUID INDEX VALUES OR AVERAGE IMPEDANCE VALUES DURING FIRST TIME PERIOD SATISFIES ADAPTIVE THRESHOLD MULTIPLIED BY CORRESPONDING WEIGHTING FACTORS

130   MODIFY IMPEDANCE SCORE WHEN FLUID INDEX VALUES OR AVERAGE IMPEDANCE VALUES DURING SECOND TIME PERIOD SATISFIES ADAPTIVE THRESHOLD MULTIPLIED BY CORRESPONDING WEIGHTING FACTORS

132   OUTPUT IMPEDANCE SCORE

FIG. 7

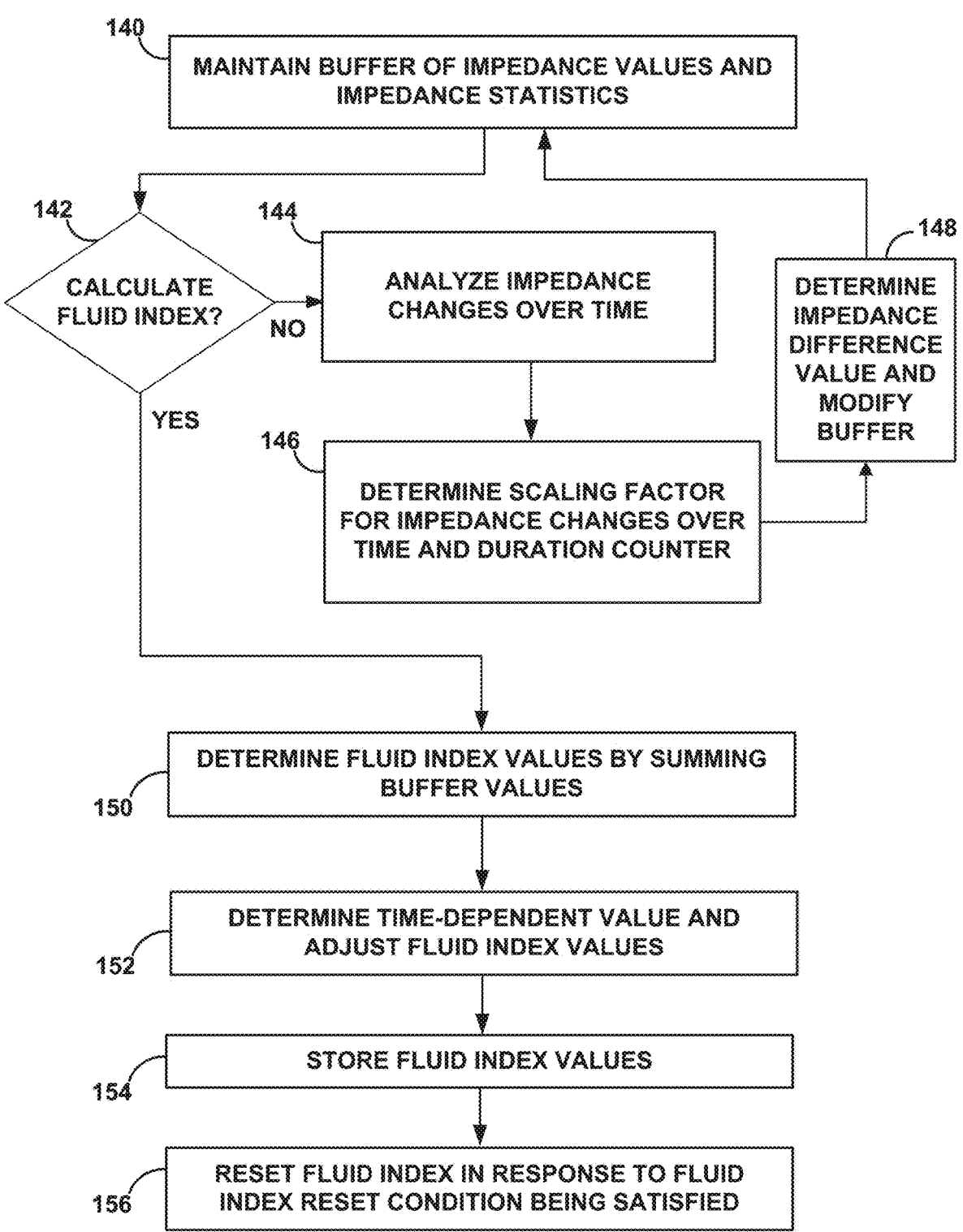

140

MAINTAIN BUFFER OF IMPEDANCE VALUES AND IMPEDANCE STATISTICS

142

CALCULATE FLUID INDEX?

144

ANALYZE IMPEDANCE CHANGES OVER TIME

NO

148

DETERMINE IMPEDANCE DIFFERENCE VALUE AND MODIFY BUFFER

YES

146

DETERMINE SCALING FACTOR FOR IMPEDANCE CHANGES OVER TIME AND DURATION COUNTER

150

DETERMINE FLUID INDEX VALUES BY SUMMING BUFFER VALUES

152

DETERMINE TIME-DEPENDENT VALUE AND ADJUST FLUID INDEX VALUES

154

STORE FLUID INDEX VALUES

156

RESET FLUID INDEX IN RESPONSE TO FLUID INDEX RESET CONDITION BEING SATISFIED

FIG. 8

DETERMINING HEALTH CONDITION STATUSES USING SUBCUTANEOUS IMPEDANCE MEASUREMENTS

This application claims the benefit of U.S. Provisional Application No. 62/906,979, entitled "DETERMINING HEALTH CONDITION STATUSES USING SUBCUTANEOUS IMPEDANCE MEASUREMENTS," filed Sep. 27, 2019, the entire contents of which are hereby incorporated in their entirety as though set forth fully herein.

CROSS-REFERENCE TO RELATED APPLICATIONS

This patent disclosure hereby incorporates by reference in its entirety the following applications filed on even date hereof; namely, U.S. Application No. 17/021,489, entitled "DETERMINING HEART CONDITION STATUSES USING SUBCUTANEOUS IMPEDANCE MEASURE-MENTS"; and U.S. Application No. 17/021,521, entitled "DETERMINING LIKELIHOOD OF AN ADVERSE HEALTH EVENT BASED ON VARIOUS PHYSIOLOGI-CAL DIAGNOSTIC STATES ".

FIELD

The disclosure relates to medical devices and, more particularly, medical devices for detecting or monitoring heart conditions.

BACKGROUND

A variety of medical devices have been used or proposed for use to deliver a therapy to and/or monitor a physiological condition of patients. As examples, such medical devices may deliver therapy and/or monitor conditions associated with the heart, muscle, nerve, brain, stomach or other organs or tissue. Medical devices that deliver therapy include medical devices that deliver one or both of electrical stimu-lation or a therapeutic agent to the patient. Some medical devices have been used or proposed for use to monitor heart failure or to detect heart failure events.

Heart Failure (HF) is the most common cardiovascular disease that causes significant economic burden, morbidity, and mortality. In the United States alone, roughly 5 million people have HF, accounting for a significant number of hospitalizations. Heart failure may result in cardiac chamber dilation, increased pulmonary blood volume, and fluid reten-tion in the lungs. Generally, the first indication that a physician has of heart failure in a patient is not until it becomes a physical manifestation with swelling or breathing difficulties so overwhelming as to be noticed by the patient who then proceeds to be examined by a physician. This is undesirable since hospitalization at such a time would likely be required for a heart failure patient to remove excess fluid and relieve symptoms.

SUMMARY

This disclosure describes techniques for providing an early warning for various heart conditions (e.g., heart failure decompensation, worsening heart failure, etc.) based on impedance measurements of subcutaneous tissue in a body of a patient. Subcutaneous impedance is an example of an impedance which may be monitored to detect worsening heart failure, e.g., changes in impedance values where changes are measured in the interstitial fluid within a subcutaneous layer of a patient. The techniques may be imple-mented by an implantable medical device (IMD) that is implanted subcutaneously, such as a leaded or non-leaded (also referred to as "leadless") subcutaneous implant, coupled to a plurality of electrodes (e.g., lead-borne elec-trodes and/or electrodes on a device housing) for measuring subcutaneous impedances.

A device (e.g., a subcutaneous IMD or a remote comput-ing device, such as a network device) compares measured impedances to reference impedances to accumulate evi-dence of changing impedance levels in the interstitium of the subcutaneous layer of a patient. This evidence is referred to as a fluid index, and may reflect a level of pulmonary or peripheral edema, increased ventricular filling pressures or other morbidities that may be associated with worsening heart failure experienced by a patient. For example, when a patient has peripheral edema related to a fluid overload condition, the patient may also have pulmonary edema related to the same fluid overload condition. As such, the subcutaneous impedance measurements and fluid index val-ues may be able to detect such fluid overloads in accordance with techniques disclosed herein.

The fluid index is one example of an index that indicates worsening heart failure. Other examples include indices or metrics of increased ventricular filling pressures or other morbidities associated with worsening heart failure experi-enced by a patient. In general, any parameter that indicates worsening heart failure may be monitored according to the techniques described herein, and an index that indicates worsening heart failure may be any index that is determined to indicate a trend in the parameter that reflects worsening heart failure, where such indices may be based on measure-ments of a parameter of a subcutaneous layer of a patient.

The reference impedance may be determined based on the previously measured impedances. In some instances, the device may represent the reference impedance as a statistical model that aims to track relative changes in impedance values over time. In another example, the device may interpolate or extrapolate impedance data, predict future data points, generate regression models for accumulated data, deploy machine learning models, etc., to determine the reference impedance value(s). For example, the reference impedance value(s) may include a mean, median, mode, and range of collected impedance information. In other examples, the reference impedance value(s) may include other useful data analytics that provide a representation of ideal or baseline impedance data points onto which a body should attempt to track, for example, when regulating cel-lular activity. The reference impedance may be based on slope values that change over time (e.g., drift-up and drift-down parameters). As discussed herein, the drift-up and drift-down parameters may change in a piece-wise linear fashion to accommodate for the rapid rise of impedance that may result in the first few months following implantation of a given 1 MB. An example reference impedance line is shown as a dashed line in FIG. 9.

In some examples, the device increments the fluid index based on the differences between measured impedances and reference impedances. In one example, the device may determine fluid index values by calculating a difference in value between daily average impedance values and a daily reference impedance value. In addition, the device may determine a fluid index value by summing or accumulating such difference values that are stored in a buffer over time. In some examples, the difference value may be modified by subtracting a variability value (e.g., a time-dependent variability value) from the difference value prior to storing the modified difference value to the buffer.

The device may modify or adjust fluid index values based on the comparison in this manner so long as the measured impedances are less than their respective reference imped- ances. The resultant fluid index may be used to determine an impedance score. In some examples, the IMD or another computing device may compare the fluid index to an adap- tive threshold to determine modifications to the impedance score. The adaptive threshold may be determined using an average (e.g., mean or median), of impedance values deter- mined within a particular time window (e.g., in the last 30 days). The adaptive threshold may also include the average (e.g., mean or median) of differences between one or more maximum impedance values and one or more minimum impedance values, or another measure of the variability of the impedance measurements, determined within a particu- lar time window (e.g., in the last 30 days). In such examples, the maximum and minimum may be the daily maximum and the daily minimum for each day. In other examples, the maximum may be the maximum in the preceding days calculated, where the average is calculated each day up to 30 days to determine the 30-day average. In another example, the average may be an average of the daily variability in measured impedance values over the course of the particular time window. In any event, the adaptive threshold may be proportional to the absolute impedance value and the intra- day variation of the impedance.

In some examples, the IMD or another computing device may compare the impedance score to one or more risk thresholds to determine whether or not to generate an alert (e.g., a notification, a status indicator, an alarm, etc.). In a non-limiting example, the alert may include text or graphics information that communicates the heart condition, e.g., heart failure, status of the patient. In some examples, the IMD may transmit the alert to another computing device. In some examples where a computing device other than the IMD determines the impedance score, that computing device may simply generate the alert or may further transmit the alert to another device. In some examples, a computing device may transmit, in response to the impedance score satisfying the one or more risk thresholds, an alert to the IMD that instructs the IMD to take some action in response to the current heart condition status. In any event, the alert may indicate status levels of a heart condition status. For example, the risk thresholds may trigger one alert for high risk, a different alert for medium risk, and yet another alert for low risk. The alerts may be communicated directly to the patient or to the clinician through a variety of methods including notifications, audible tones, handheld devices and automatic or on-demand telemetry to computerized commu- nication network. In some examples, the alert may include an alarm, such as an audible alarm or visual alarm.

Various techniques are used to enable the fluid index and the impedance score to accurately represent changes in patient condition over time, and enable the alerts to better correspond to a clinically significant worsening of patient condition. In some examples, the techniques involve varying a parameter that affects a slope of the index over time, to address time-dependent factors or other factors that may affect the accuracy of the fluid index.

In some examples, the amount of incrementing is reduced based on a variability of the measured impedances. Accu- mulating the fluid index less in the presence of high vari- ability may facilitate accuracy of the fluid index by lessening accumulation during periods of impedance instability that are not directly associated with worsening heart failure.

Increasing the accumulation over time may allow consis- tently decreasing impedances to more quickly result in an alert.

In some examples, the manner in which the reference impedances are determined changes over time. In particular, amounts by which the reference impedance may be incre- mented or decremented may be different days after implan- tation, and then may change over time. In this manner, the reference impedance may be able to respond to rapid changes (e.g., increases in impedance that are commonly observed after implantation), or respond after surgical modi- fication of the implanted system, such as lead change/ revision or device change.

In some examples, a device adaptively calculates the fluid index over time by accumulating the fluid index based on a finite number of previous comparisons between measured impedances and reference impedances, e.g., over a finite period of time, such as the last X days. For example, a device may sum a finite number of differences between measured and reference impedances, which may be stored in a first- in-first-out (FIFO) buffer of finite size. The finite number of comparisons may act as a sliding window with respect to previous comparisons. By limiting the number of compari- sons used to determine the fluid index using finite memory, the fluid index may be more sensitive to recent events involving changes in the subcutaneous tissue impedance, as opposed to events occurring outside of the sliding time window. Such algorithms may provide more accurate rep- resentations of a health condition status of a patient on a given day. As will be further described, such algorithms may be further improved by accumulating the fluid index less in patients having higher day-to-day variability in impedance values due to clinically insignificant impedance shifts and temporary impedance deviations due to, for example, poor adherence to medication regimens or diet restrictions. Alert- ing in response to such relatively less significant events is also limited. Moreover, limiting the accumulation of the fluid index in this manner may limit alerting to be in response to more recent events, e.g., to avoid alerting due to past compliance issues which may have been resolved.

As discussed herein, determining an impedance score using subcutaneous impedance involves determining the absolute value of the impedance and relative changes in impedance. The device may determine an impedance score using the fluid index values and the average impedance determined over time. The impedance score may serve as a valuable indicator for a heart condition status of a patient or other health condition status of a patient (e.g., edema, preeclampsia, hypertension, etc.). The impedance score may increment or decrement by a first amount (e.g., one point) under certain circumstances and increment or decrement by a second amount (e.g., two points) under other circum- stances.

In some examples, the impedance score is compared to two thresholds to provide hysteresis in the alert decision. An alert is generated when the impedance score crosses a first, higher threshold. The alert is ended when the impedance score subsequently crosses a second, lower threshold. By generating alerts in this manner, a device may generate fewer "sporadic" alerts that may be misinterpreted by the patient or a clinician when the impedance score fluctuates near the higher, alert threshold value. In addition, the device may provide multiple alerts of varying degrees relating to risk level. For example, the alerts may have hysteresis thresholds for a high risk, medium risk, and/or low risk thresholds.

In one example, the disclosure provides a system for detecting statuses of health conditions. The system includes an implantable medical device (IMD) including a plurality of electrodes and configured for subcutaneous implantation, wherein the IMD is configured to receive one or more subcutaneous tissue impedance signals from the electrodes. The IMD is configured to receive one or more subcutaneous tissue impedance signals. The system further includes processing circuitry configured to at least determine, based at least in part on the one or more subcutaneous tissue impedance signals, a plurality of tissue impedance values. The processing circuitry is further configured to at least determine, based at least in part on the plurality of tissue impedance values, a fluid index value and an average impedance value. The processing circuitry is further configured to at least determine an impedance score based at least in part on the fluid index value and the average impedance value. The processing circuitry is further configured to at least determine a health condition status of the patient based at least in part on the impedance score. The processing circuitry is further configured to at least identify a fluid index reset condition and reset the fluid index value to a baseline value in response to identifying the fluid index reset condition.

In another example, the disclosure provides a method of detecting statuses of health conditions, the method including determining, based at least in part on one or more subcutaneous tissue impedance signals, a plurality of tissue impedance values, the one or more subcutaneous tissue impedance signals received from at least one electrode of an implantable medical device (IMD) disposed in a subcutaneous layer of a patient, determining, based at least in part on the plurality of tissue impedance values, a fluid index value and an average impedance value, determining an impedance score based at least in part on the fluid index value and average impedance value, determining a health condition status of the patient based at least in part on the impedance score. The method further includes identifying a fluid index reset condition and resetting the fluid index value to a baseline value in response to identifying the fluid index reset condition.

In another example, the disclosure provides a computer-readable storage-medium having stored thereon instructions that, when executed, cause one or more processors to at least determine, based at least in part on one or more subcutaneous tissue impedance signals, a plurality of tissue impedance values, determine, based at least in part on the plurality of tissue impedance values, a fluid index value and an average impedance value, determine an impedance score based at least in part on the fluid index value and average impedance value, determine a health condition status based at least in part on the impedance score, identify a fluid index reset condition, and reset the fluid index value to a baseline value.

The disclosure also provides means for performing any of the techniques described herein, as well as non-transitory computer-readable media including instructions that cause a programmable processor to perform any of the techniques described herein.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

6

BRIEF DESCRIPTION OF THE DRAWINGS

FIG. 6 is a flow diagram illustrating an example operation for determining a heart condition status of a patient, in accordance with one or more techniques disclosed herein.

FIG. 7 is a flow diagram illustrating an example operation for determining an impedance score based on subcutaneous tissue impedance values, in accordance with one or more techniques disclosed herein.

FIG. 8 is a flow diagram illustrating an example operation for determining a fluid index based on subcutaneous tissue impedance values, in accordance with one or more techniques disclosed herein.

Like reference characters denote like elements throughout the description and figures.

DETAILED DESCRIPTION

Figure 1:
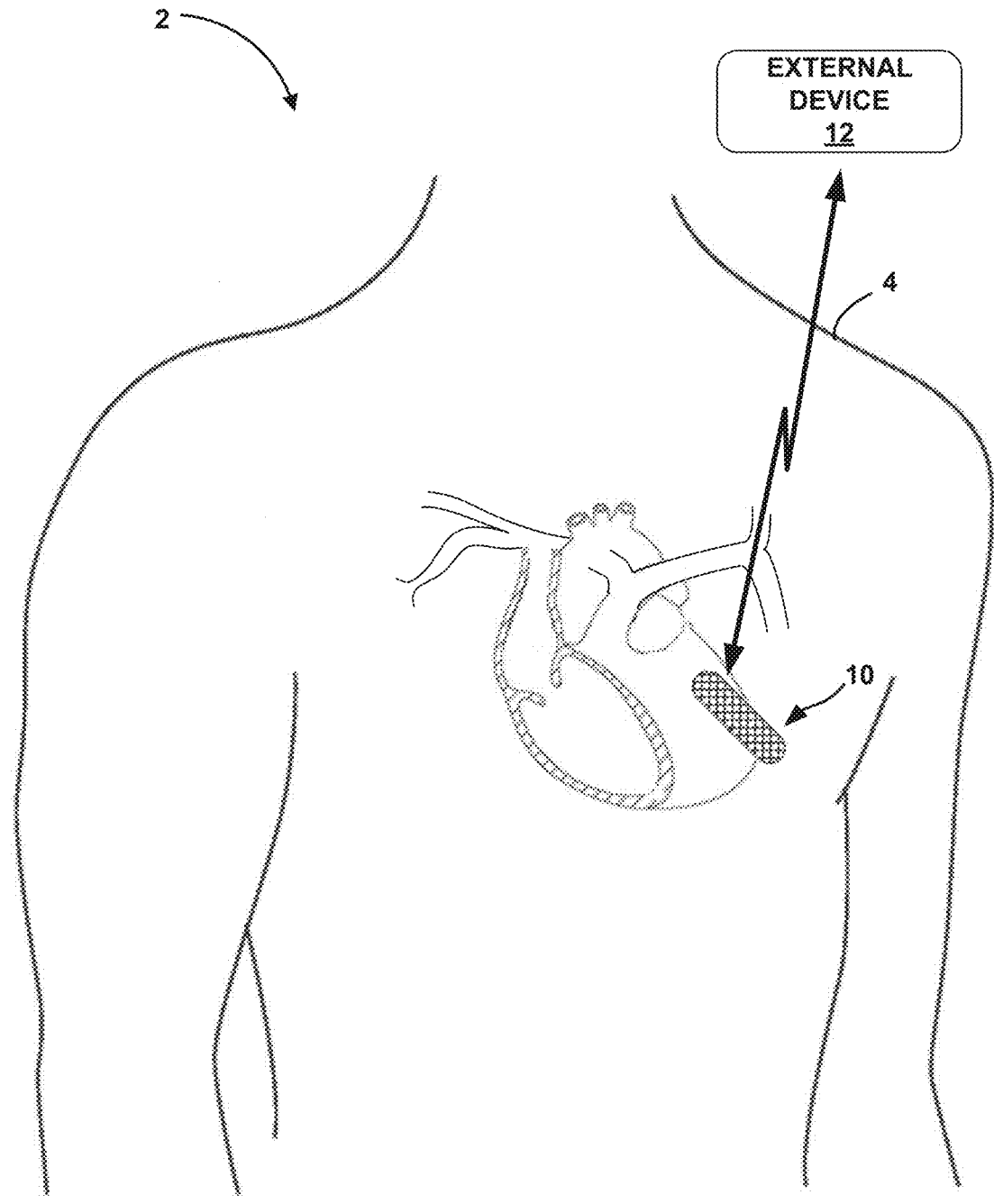
FIG. 1 illustrates the environment of an example medical system in conjunction with a patient.
Figure 2:
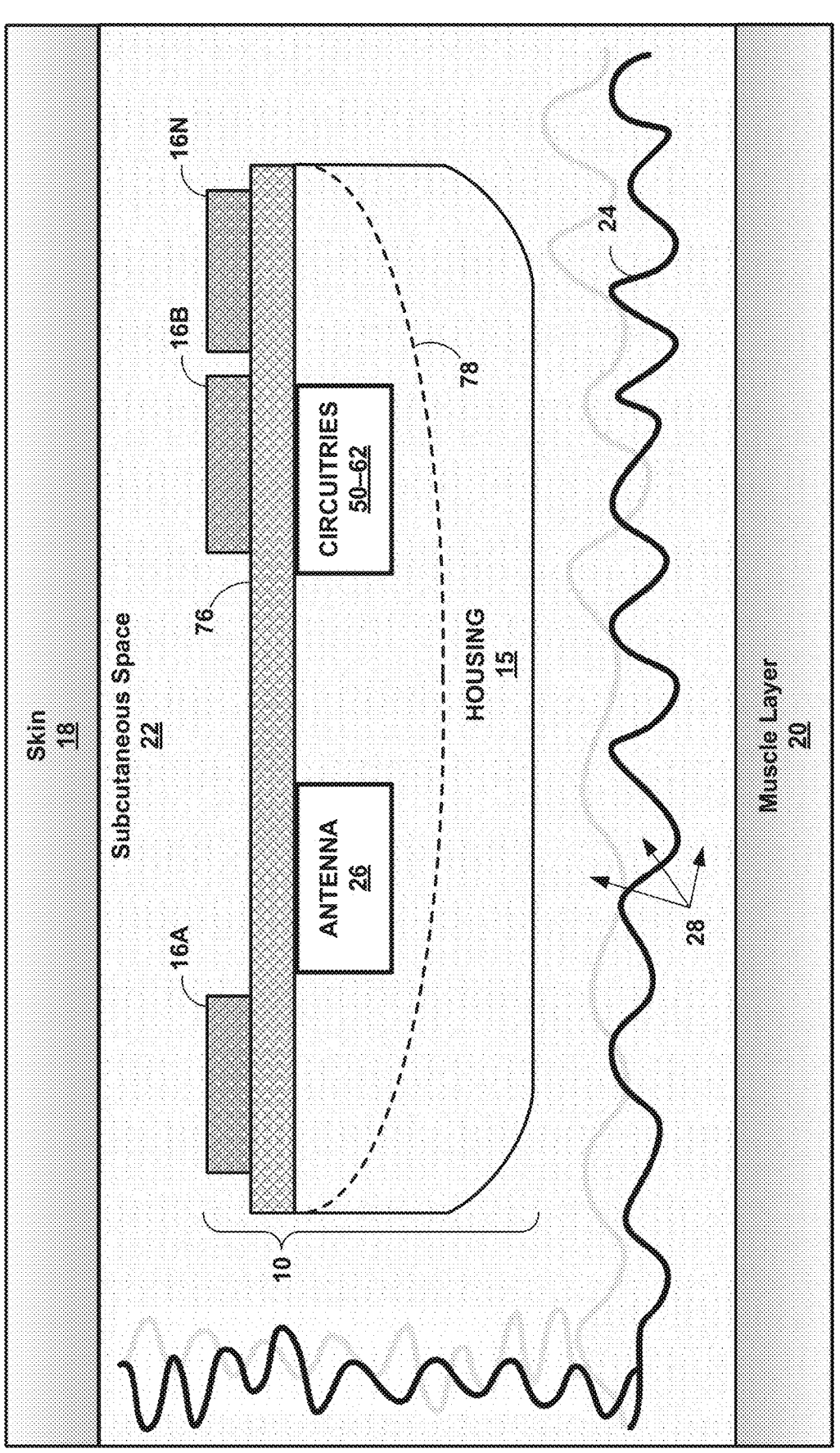
FIG. 2 is a conceptual side-view diagram illustrating an implantable medical device (IMD) of the example medical system of FIG. 1, in accordance with one or more techniques disclosed herein.

In general, impedance measurements taken via electrodes in the subcutaneous space, e.g., electrodes on a subcutaneously implanted medical device as shown in FIGS. 1 and 2, may be measurements of the impedance of interstitial fluid and subcutaneous tissue. In an example, during a heart failure decompensation event, reduction in cardiac output can tend to increase venous pressure. An increase in venous pressure tends to lead to an increase in pressure with respect to capillaries compared to the interstitial space. The combination of such tendencies may then lead to a net outflow of fluid from the capillaries into the interstitium or interstitial space of a patient. In such instances, the interstitium will have an increase in fluid accumulation. An increase in fluid accumulation tends to provide a reduction in impedance measured between electrodes.

Implantable medical devices (IMDs) can sense and monitor impedance signals and use those signals to determine a heart condition status of a patient or other health condition status of a patient (e.g., edema, preeclampsia, hypertension, etc.). The electrodes used by IMDs to sense impedance signals are typically integrated with a housing of the IMD and/or coupled to the IMD via one or more elongated leads. Example IMDs that include electrodes include the Reveal LINQ™ Insertable Cardiac Monitor (ICM), developed by Medtronic, Inc., of Minneapolis, Minn., which may be inserted subcutaneously. Such IMDs may facilitate relatively longer-term monitoring of patients during normal daily activities and may periodically transmit collected data to a network service, such as the Medtronic CareLink® Network, developed by Medtronic, Inc., of Minneapolis, Minn.

Medical devices configured to measure impedance via implanted electrodes, including the examples identified herein, may implement the techniques of this disclosure for measuring impedance changes in the interstitial fluid of a patient to determine whether the patient is experiencing worsening heart failure or decompensation. The techniques include evaluation of the impedance values using criteria configured to provide a desired sensitivity and specificity of heart failure detection. The techniques of this disclosure for identifying heart failure worsening may facilitate determinations of cardiac wellness and risk of sudden cardiac death and may lead to clinical interventions to suppress heart failure worsening, such as with medications.

FIG. 1 illustrates the environment of an example medical system 2 in conjunction with a patient 4, in accordance with one or more techniques of this disclosure. Patient 4 ordinarily, but not necessarily, will be a human. For example, patient 4 may be an animal needing ongoing monitoring for cardiac conditions. System 2 includes implantable medical device (IMD) 10. IMD 10 may include one or more electrodes (not shown) on its housing, or may be coupled to one or more leads that carry one or more electrodes. System 2 may also include external device 12. Example system 2 may be used to measure subcutaneous impedance to provide to patient 4 other users an early warning for the onset of a heart failure decompensation event.

The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1). Accordingly, IMD 10 may include a plurality of electrodes and may be configured for subcutaneous implantation (e.g., outside of a thorax of patient 4) or in other regions of the body of patient 4, as well.

IMD 10 is configured to measure impedance values within the interstitial fluid of patient 4. For example, IMD 10 may be configured to receive one or more signals indicative of subcutaneous tissue impedance electrodes. In some examples, IMD 10 may be a purely diagnostic device. For example, IMD 10 may be a device that only measures subcutaneous impedance values of patient 4. IMD 10 may also use the impedance value measurements to determine one or more fluid index values, impedance scores, and/or various thresholds, such as adaptive thresholds, scoring thresholds, weighting factors for thresholds, and/or cardiac risk thresholds.

Subcutaneous impedance may be measured by delivering a signal through an electrical path between electrodes (not shown in FIG. 1). In some examples, the housing of IMD 10 may be used as an electrode in combination with electrodes located on leads. For example, system 2 may measure subcutaneous impedance by creating an electrical path between a lead and one of the electrodes. In additional examples, system 2 may include an additional lead or lead segment having one or more electrodes positioned subcutaneously or within the subcutaneous layer for measuring subcutaneous impedance. In some examples, two or more electrodes useable for measuring subcutaneous impedance may be formed on or integral with the housing of IMD 10.

System 2 measures subcutaneous impedance of patient 4 and processes impedance data to accumulate evidence of decreasing impedance. The accumulated evidence is referred to as a fluid index and may be determined as function of the difference between measured impedance values and reference impedance values. The fluid index may then be used to determine impedance scores that are indicative of a heart condition of patient 4. For example, an impedance score may be measured against a cardiac risk threshold that identifies high risk, medium risk, or low risk of a worsening heart condition.

In some examples, IMD 10 may also sense cardiac electrogram (EGM) signals via the plurality of electrodes and/or operate as a therapy delivery device. For example, IMD 10 may additionally operate as a therapy delivery device to deliver electrical signals to the heart of patient 4, such as an implantable pacemaker, a cardioverter, and/or defibrillator, a drug delivery device that delivers therapeutic substances to patient 4 via one or more catheters, or as a combination therapy device that delivers both electrical signals and therapeutic substances.

In some examples, system 2 may include any suitable number of leads coupled to IMD 10, and each of the leads may extend to any location within or proximate to a heart or in the chest of patient 4. For example, other examples therapy systems may include three transvenous leads and an additional lead located within or proximate to a left atrium of a heart. As other examples, a therapy system may include a single lead that extends from IMD 10 into a right atrium or right ventricle, or two leads that extend into a respective one of a right ventricle and a right atrium.

In some examples, IMD 10 may be implanted subcutaneously in patient 4. Furthermore, in some examples, external device 12 may monitor subcutaneous impedance values according to the techniques described herein. In some examples, IMD 10 takes the form of the Reveal LINQ™ ICM, or another ICM similar to, e.g., a version or modification of, the LINQ™ ICM, which may be inserted subcutaneously. Such IMDs may facilitate relatively longer-term monitoring of patients during normal daily activities, and may periodically transmit collected data to a network service, such as the Medtronic CareLink® Network.

External device 12 may be a computing device with a display viewable by a user and an interface for providing input to external device 12 (i.e., a user input mechanism). The user, may be a physician technician, surgeon, electrophysiologist, clinician, or patient 4. In some examples, external device 12 may be a notebook computer, tablet computer, computer workstation, one or more servers, cellular phone, personal digital assistant, handheld computing device, networked computing device, or another computing device that may run an application that enables the computing device to interact with IMD 10. External device 12 is configured to communicate with IMD 10 and, optionally, another computing device (not illustrated in FIG. 1), via wired or wireless communication. External device 12, for example, may communicate via near-field communication (NFC) technologies (e.g., inductive coupling, NFC or other communication technologies operable at ranges less than 10-20 cm) and far-field communication technologies (e.g., Radio Frequency (RF) telemetry according to the 802.11 or Bluetooth® specification sets, or other communication technologies operable at ranges greater than NFC technologies).

In some examples, external device 12 may include a programming head that may be placed proximate to the body of patient 4 near the IMD 10 implant site in order to improve the quality or security of communication between IMD 10 and external device 12.

External device 12 may be coupled to external electrodes, or to implanted electrodes via percutaneous leads. In some examples, external device 12 may monitor subcutaneous tissue impedance measurements from IMD 10, according to the techniques described herein.

The user interface of external device 12 may receive input from the user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. External device 12 can additionally or alternatively include a peripheral pointing device, such as a mouse, via which the user may interact with the user interface. In some examples, a display of external device 12 may include a touch screen display, and a user may interact with external device 12 via the display. It should be noted that the user may also interact with external device 12 remotely via a networked computing device.

External device 12 may be used to configure operational parameters for IMD 10. For example, external device 12 may provide a parameter resolution for IMD 10 that indicates a resolution of data that IMD 10 should be obtaining. Examples of resolution parameters may include a frequency at which the electrodes process impedance measurements or a frequency at which impedance measurements should be considered in determining the heart condition status of a patient. In some examples, resolution parameters include filters that specify what type of data or quality of data should flow into the determination of a heart condition status of a patient. For example, the type of data may specify that the impedance measurements collected during a certain time period (e.g., daytime, nighttime, high activity, low activity, etc.) should be excluded from the status determination, such as by determining statistical representations of historical data through use of non-excluded data. The quality of data may refer to any characteristic used to characterize obtained signal measurements, such as signal-to-noise ratios (SNRs), duplicate data entries, weak signal readings, etc.

In some examples, the user may use external device 12 to program impedance measurement parameters, such as to select electrodes used to measure subcutaneous impedance and select waveforms for measuring subcutaneous impedance, or to program scoring parameters, threshold parameters, and/or resolution parameters. External device 12 may also be used to program a therapy progression, select electrodes to deliver defibrillation pulses, select waveforms for the defibrillation pulse, or select or configure a fibrillation detection algorithm for IMD 10. The user may also use external device 12 to program aspects of other therapies provided by IMD 10, such as cardioversion or pacing therapies. In some examples, the user may activate certain features of IMD 10 by entering a single command via external device 12, such as depression of a single key or combination of keys of a keypad or a single point-and-select action with a pointing device.

External device 12 may be used to retrieve data from IMD 10. The retrieved data may include impedance values measured by IMD 10, impedance scores determined by IMD 10, values of physiological parameters measured by IMD 10, indications of episodes of arrhythmia or other maladies detected by IMD 10, and physiological signals recorded by IMD 10. For example, external device 12 may retrieve information related to detection of a sudden impedance shift by IMD 10, such as a count or other quantification of impedance fluctuation, e.g., over a time period since the last retrieval of information by external device 12. External device 12 may also retrieve cardiac EGM segments recorded by IMD 10, e.g., due to IMD 10 determining that an episode of arrhythmia or another malady occurred during the segment, or in response to a request to record the segment from patient 4 or another user.

In some examples, the user may use external device 12 to retrieve information from IMD 10 regarding other sensed physiological parameters of patient 4, such as activity or posture. As discussed herein (e.g., with reference to FIG. 5), one or more remote computing devices may interact with IMD 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques of this disclosure for measuring subcutaneous impedance values, e.g., in the interstitial fluid, to determine heart condition statuses. In some examples, the processing circuitry of medical system 2 analyzes impedance values sensed by IMD 10 to determine whether a change in impedance of the interstitial fluid satisfy a plurality of criteria. As discussed herein, the criteria may include noise criteria, inter-depolarization interval (e.g., R-R interval) criteria, morphological criteria, fluid index criteria, and/or impedance scoring criteria.

Although described in the context of examples in which IMD 10 includes an insertable or implantable IMD, example systems including one or more external devices of any type configured to sense subcutaneous tissue impedances may be configured to implement the techniques of this disclosure. In some examples, IMD 10 or an external device 12 may use one or more of subcutaneous tissue impedance measurements and intra-vascular impedance. In some examples, processing circuitry of the external device or of IMD 10 may receive intra-vascular impedance measurements. In an example, IMD 10 may be configured to measure intra-vascular impedance and transmit the intra-vascular impedance to an external device 12 or store the intra-vascular impedance measurements locally to IMD 10.

Intravascular measurements, as measured by intra-thoracic impedance, measures intravascular volume. Subcutaneous impedance measures interstitial volume. In general, interstitial spaces are essentially reservoirs for extra intravascular volume. When intravascular volume increases, the balance between hydrostatic pressure and osmotic pressure may change (e.g., hydrostatic pressure becomes greater than osmotic pressure). In addition, fluid shifts from intravascular to extravascular or interstitial space (e.g., peripheral edema, pulmonary congestion, etc.). The reverse may happen when the intravascular volume decreases, such as during dialysis. In such instances, osmotic pressure may become greater than hydrostatic pressure. In addition, fluid from the interstitial space tends to flows back into the intravascular space. In addition, sweating and the lymphatic system can also drain the interstitial space. Also the splanchnic system acts as a quicker balance mechanism compared to interstitial space.

Various health conditions provide such responses as described above, and with a delay in the response. The delay may indicate whether the patient is more or less sick. The osmotic pressure depends on electrolyte balance and that changes with severity of disease. Also, in cases like right heart failure or pulmonary hypertension the pattern of changes (e.g., net filtration rate) in intravascular to intersti-tial volume may be significantly different compared to acute decompensated heart failure. In some instances, the opposite may occur as well (e.g., interstitial fluid decreases but intravascular fluid increases), such as when a patient is taking certain types of medications. Vasodilating then increases extravascular capacity and the sodium (e.g., elec-trolyte balance changes) such that more fluid is pulled back into the intravascular space from extravascular space. Thus, IMD 10 or external device 10 may monitor for efficacy of such drugs or degrees of vaconstriction/vasodilation, or monitor when sufficient fluid has been removed by dialysis, etc. based on an impedance score determined in accordance with one or more of the various techniques of this disclosure.

In some examples, IMD 10 or external device 12 may determine an impedance score using one or more of the intra-vascular impedance measurements and subcutaneous tissue impedance measurements (e.g., tissue impedance val-ues). For example, intra-vascular impedance measurements may be used to determine the fluid index values. In some examples, IMD 10 or external device 12 may determine fluid index values from one or more of the intra-vascular imped-ance measurements or subcutaneous impedance measure-ments. For example, IMD 10 or external device 12 may average together fluid index values based intra-vascular impedance and fluid index values based on subcutaneous impedance. In other examples, intra-vascular impedance may be used to determine an impedance score similar to how subcutaneous impedance is used in accordance with tech-niques of this disclosure. The impedance scores may be combined, such as by averaging the impedance scores, in order to determine an impedance score for patient 4. In some examples, IMD 10 may transmit the impedance score for patient 4, and/or raw data used to determine the impedance score, to external device 12 for subsequent use, and vice versa.

In some examples, IMD 10 may have one or more electrodes disposed within one layer of patient 4 (e.g., subcutaneous layer), whereas at least one other electrode may be disposed within another layer of patient 4 (e.g., dermis layer, muscle layer, etc.). In such instances, IMD 10 may track shifts in impedance values in accordance with certain impedance scoring techniques, regardless of whether the impedance values are measured using electrodes 16 where one of electrodes 16 is disposed within a tissue layer other than the subcutaneous layer.

System 2 provides an alert to patient 4 and/or other users when the fluid index indicates the onset of a heart failure decompensation event. The process for determining when to alert patient 4 involves comparing the fluid index to one or more threshold values and is described herein. The alert may be an audible alert generated by IMD 10 and/or external device 12, a visual alert generated by external device 12, such as a text prompt or flashing buttons or screen, or a tactile alert generated by IMD 10 and/or external device 12 such as a vibration or vibrational pattern. Furthermore, the alert may be provided to other devices, e.g., via a network. Several different levels of alerts may be used based on the level of risk detected through the techniques described herein.

In examples in which IMD 10 also operates as a pace-maker, a cardioverter, and/or defibrillator, or otherwise monitors the electrical activity of the heart, IMD 10 may sense electrical signals attendant to the depolarization and repolarization of the heart of patient 4 via electrodes coupled to at least one lead. In some examples, IMD 10 can provide pacing pulses to the heart of patient 4 based on the electrical signals sensed within the heart of patient 4. The configura-tions of electrodes used by IMD 10 for sensing and pacing may be unipolar or bipolar. IMD 10 may also provide defibrillation therapy and/or cardioversion therapy via elec-trodes located on at least one lead, as well as a housing electrode. IMD 10 may detect arrhythmia of the heart of patient 4, such as fibrillation of ventricles, and deliver defibrillation therapy to the heart of patient 4 in the form of electrical pulses. In some examples, IMD 10 may be pro-grammed to deliver a progression of therapies, e.g., pulses with increasing energy levels, until a fibrillation of the heart of patient 4 is stopped. IMD 10 detects fibrillation employ-ing one or more fibrillation detection techniques known in the art.

FIG. 2 is a conceptual side-view diagram illustrating an example configuration of IMD 10 of FIG. 1. The conceptual side-view diagram illustrates a muscle layer 20 and a skin layer 18. The region between muscle layer 20 and skin layer 18 includes subcutaneous space 22. Subcutaneous space includes blood vessels 24, such as capillaries, arteries, or veins, and interstitial fluid in the interstitium 28 of subcu-taneous space 22. Subcutaneous space 22 has interstitial fluid that is commonly found between skin layer 18 and muscle layer 20. Subcutaneous space 22 may include inter-stitial fluid that surrounds blood vessels 24. For example, interstitial fluid surrounds capillaries and allows the passing of capillary elements (e.g., nutrients) between the different layers of a body through interstitium 28. In some examples, IMD 10 may sense impedance changes with respect to interstitial fluid. In another example, IMD 10 may sense impedance changes with respect to extravascular fluid and other conductive tissues proximate to electrodes 16. In any event, IMD 10 may track shifts or changes in impedances of these layers, regardless of which conductive tissue layer and/or type of fluid, because impedance changes occur during adverse health events, such as worsening heart fail-ure, even where some of electrodes 16 are positioned in layers other than subcutaneous space 22 or in contact with fluids other than interstitial fluid.

In the example shown in FIG. 2, IMD 10 may include a leadless, subcutaneously-implantable monitoring device having a housing 15 and an insulative cover 76. Electrodes 16A-16N (collectively, "electrodes 16") may be formed or placed on an outer surface of cover 76. Although the illustrated example includes three electrodes 16, IMDs including or coupled to more or less than three electrodes 16 may implement the techniques of this disclosure in some examples. For example, electrode 16N or additional elec-trodes may be unnecessary in some instances, e.g., in which housing 15 is conductive and acts as an electrode of IMD 10. Circuitries 50-62, described below with reference to FIG. 3, may be formed or placed on an inner surface of cover 76, or within housing 15. In the illustrated example, antenna 26 is formed or placed on the inner surface of cover 76, but may be formed or placed on the outer surface in some examples. In some examples, one or more of sensors 62 may be formed or placed on the outer surface of cover 76. In some examples, insulative cover 76 may be positioned over an open housing 15 such that housing 15 and cover 76 enclose antenna 26 and circuitries 50-62, and protect the antenna and circuitries from fluids such as interstitial fluids or other bodily fluids.

IMD 10 can face outward toward skin layer 18, inward toward muscle layer 20, or perpendicular in any direction (e.g., left, right, into the page of FIG. 2, out of the page of FIG. 2). For example, IMD 10 may be oriented to face outward toward the skin, as shown in FIG. 2. In some examples, IMD 10 may be oriented vertically relative to the skin layer 18 and muscle layer 20 such that the electrodes face to the left of the page of FIG. 2 or to the right of the page of FIG. 2. In other examples, IMD 10 may be oriented diagonally or horizontally (as shown in FIG. 2). Although shown with a particular orientation in FIG. 2, a person of skill in art would understand that IMD 10 can have various orientations and that the orientation in FIG. 2 is for illustrative purposes. Similarly, a person of skill in the art would understand that IMD 10 may be positioned closer to muscle layer 20 than to an outer layer of skin layer 18 (e.g., dermis layer or epidermis layer), whereas at other times, IMD 10 may be closer to an outer layer of skin layer 18 (e.g., dermis layer or epidermis layer).

IMD 10 may also be any shape (e.g., circular, square, rectangular, trapezoidal, etc.). For example, as shown in FIG. 2, IMD 10 has a particular shape having rounded edges across the housing 15. In addition, electrodes 16 may be positioned around the perimeter of the shape or around a partial perimeter of the shape (as shown in FIG. 2). In some instances, the configuration of electrodes 16 is selected so as to maximize the accuracy of the impedance measurements based on a relative location of circuitries 50-62. The location of circuitries 50-62 may be based on form factor and other considerations (charging, electromagnetic noise reduction, etc.) such that electrodes 16 may be positioned as an indirect effect of the selected configuration of circuitries 50-62. In other examples, electrodes may be positioned irrespective of the configuration of circuitries 50-62 and instead, may be based on other design considerations such as the relative locations of blood vessels 24 within an implant region. For example, electrodes 16 may be positioned so as to face a capillary of interest or group of capillaries that may be utilized to provide an even more accurate depiction of impedance changes over time. For instance, IMD 10 may determine that an optimal impedance reading is available nearer certain blood vessels 24 compared to other blood vessels 24. IMD 10 may have allow for self-repositioning to take advantage of the optimal reading, for example, through remote control operations, magnetic repositioning, etc. For example, IMD 10 may receive a remote-control signal or magnetic impulse causing IMD 10 to rotate in a desired direction (clockwise, counterclockwise, etc.) in order to achieve such optimal readings.

IMD 10 may be configured to float within interstitium 28 or may be fixed in place, for example, using lead wires as a tether allowing controlled degrees of freedom depending on the lead wire configuration. For example, lead wires having more slack may allow IMD 10 more degrees of freedom to float within interstitium 28.

In some examples, at least one of electrodes 16 of IMD 10 may disposed within another layer, such as muscle layer 20 or skin layer 18. In other examples, electrodes 16 may be disposed all within a single layer, such as subcutaneous space 22. In any event, at least one of electrodes 16 will contact interstitial fluid in subcutaneous space 22, whereas other electrodes 16 may not contact interstitial fluid. In other examples, each of electrodes 16 or at least two of electrodes 16 will contact interstitial fluid in subcutaneous space 22. In addition, at least two of the electrodes 16 may be positioned approximately 3 cm-5 cm apart, such as at 4 cm apart. In another example, some or all of electrodes 16 may be positioned closer or farther away than 4 cm.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 3:
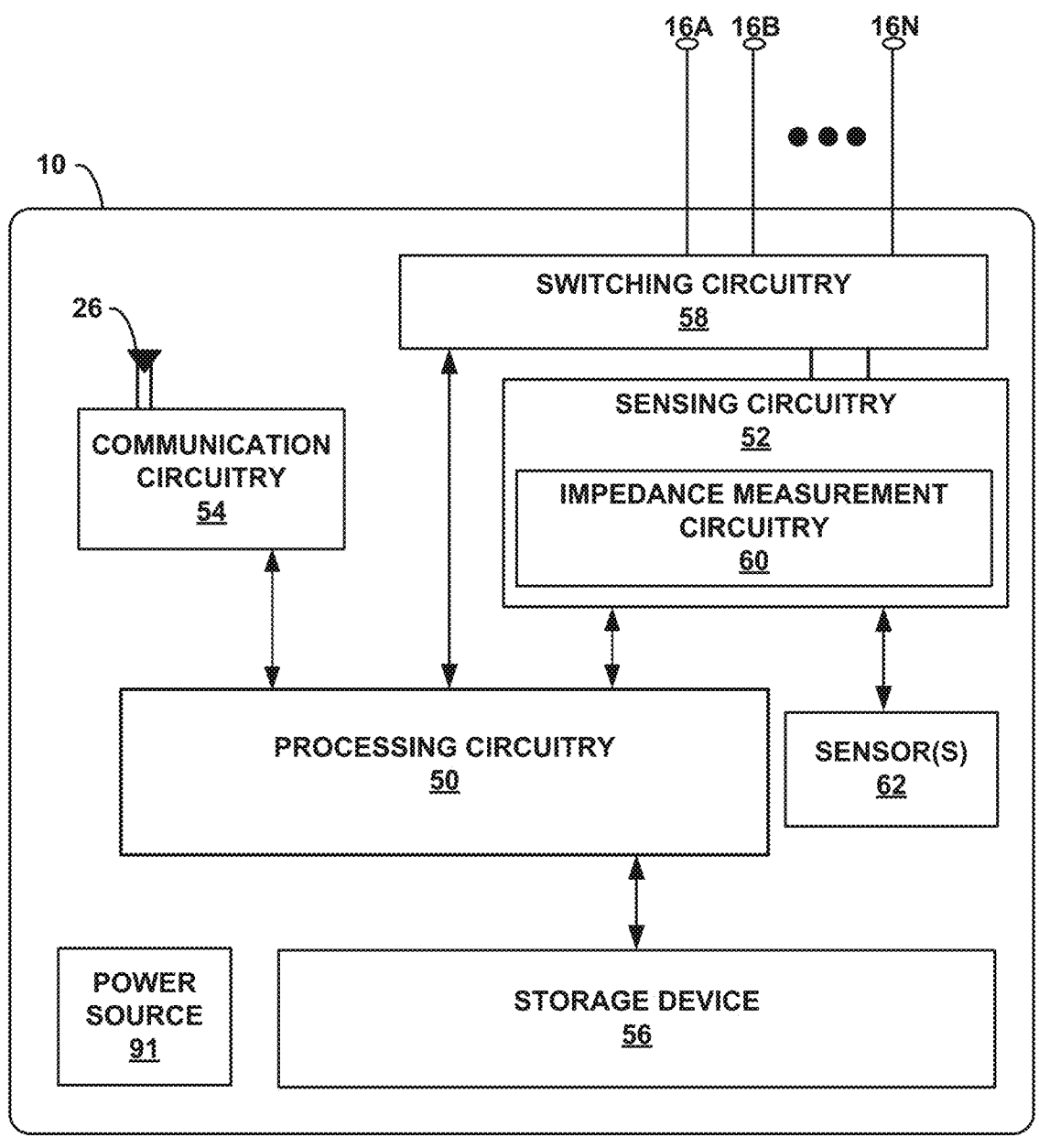
FIG. 3 is a functional block diagram illustrating an example configuration of the IMD of FIGS. 1 and 2, in accordance with one or more techniques disclosed herein.

FIG. 3 is a functional block diagram illustrating an example configuration of an IMD, such as IMD 10 described with reference to FIGS. 1 and 2. In the illustrated example, IMD 10 includes electrodes 16, antenna 26, processing circuitry 50, sensing circuitry 52, impedance measurement circuitry 60, communication circuitry 54, storage device 56, switching circuitry 58, sensors 62, and power source 91.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense impedance and/or cardiac signals, as controlled by processing circuitry 50. Sensing circuitry 52 may sense signals from electrodes 16, e.g., to produce a cardiac EGM or subcutaneous electrocardiogram (ECG), in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

In some examples, processing circuitry 50 may use switching circuitry 58 to select, e.g., via a data/address bus, which of the available electrodes are to be used to obtain impedance measurements of interstitial fluid. Switching circuitry 58 may include a switch array, switch matrix, multiplexer, transistor array, microelectromechanical switches, or any other type of switching device suitable to selectively couple sensing circuitry 58 to selected electrodes. In some examples, sensing circuitry 52 includes one or more sensing channels, each of which may include an amplifier. In response to the signals from processing circuitry 50, switching circuitry 58 may couple the outputs from the selected electrodes to one of the sensing channels.

In some examples, one or more channels of sensing circuitry 52 may include R-wave amplifiers that receive signals from electrodes 16. In some examples, the R-wave amplifiers may take the form of an automatic gain-controlled amplifier that provides an adjustable sensing threshold as a function of the measured R-wave amplitude. In addition, in some examples, one or more channels of sensing circuitry 52 may include a P-wave amplifier that receives signals from electrodes 16. Sensing circuitry may use the received signals for pacing and sensing in the heart of patient 4. In some examples, the P-wave amplifier may take the form of an automatic gain-controlled amplifier that provides an adjustable sensing threshold as a function of the measured P-wave amplitude. Other amplifiers may also be used. In some examples, sensing circuitry 52 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in storage device 56. Processing circuitry 50 may employ digital signal analysis techniques to characterize the digitized signals stored in storage device 56 to detect and classify cardiac arrhythmias from the digitized electrical signals.

Sensing circuitry 52 includes impedance measurement circuitry 60. Processing circuitry 50 may control impedance circuitry 60 to periodically measure an electrical parameter to determine an impedance, such as a subcutaneous impedance indicative of fluid found in interstitium 28. For a subcutaneous impedance measurement, processing circuitry 50 may control impedance measurement circuitry 60 to deliver an electrical signal between selected electrodes 16 and measure a current or voltage amplitude of the signal. Processing circuitry 50 may select any combination of electrodes 16, e.g., by using switching circuitry 58 and sensing circuitry 52. Impedance measurement circuitry 60 includes sample and hold circuitry or other suitable circuitry for measuring resulting current and/or voltage amplitudes. Processing circuitry 50 determines an impedance value from the amplitude value(s) received from impedance measurement circuitry 60. In some examples, processing circuitry 50 may include switching circuitry 58 to switch between measurements of ECG and impedance measurements across the same electrodes 16. For example, switching circuitry 58 may use multiplexing to switch between measurements, such that processing circuitry 50 may utilize electrodes 16 to perform various measurements (e.g., impedance, ECG, etc.). In such examples, processing circuitry 50 may receive a plurality of signals using electrodes 16, where the signals include at least one ECG and/or one or more subcutaneous tissue impedance signals. That is, the same electrode may be used to measure ECG and impedance. Such parameters may be measured together. In such examples, IMD 10 may utilize such ECG information measured using ECG measurements or features derived from ECG (e.g., heart rate, r-wave amplitude, etc.). In an example, IMD 10 may combine the ECG information with subcutaneous impedance to identify risk for heart failure, such as by using a Bayesian analysis, as in U.S. Application No. 62/906,991 entitled "DETERMINING LIKELIHOOD OF AN ADVERSE HEALTH EVENT BASED ON VARIOUS PHYSIOLOGICAL DIAGNOSTIC STATES," incorporated herein by reference in its entirety.

In some examples, IMD 10 may include measurement circuitry having an amplifier design configured to switch in real-time and continuously between impedance value measurements and other physiological parameter measurements, such as ECG. In addition, IMD 10 may enable impedance measurement circuitry 60 for short periods of time in order to conserve power. In one example, IMD 10 may use an amplifier circuit, such as a chopper amplifier, according to certain techniques described in U.S. application Ser. No. 12/872,552 by Denison et al., entitled "CHOPPER-STABI-LIZED INSTRUMENTATION AMPLIFIER FOR IMPED-ANCE MEASUREMENT," filed on Aug. 31, 2010, incorporated herein by reference in its entirety.

Because either IMD 10 or external device 12 may be configured to include sensing circuitry 52, impedance measurement circuitry 60 may be implemented in one or more processors, such as processing circuitry 50 of IMD 10 or processing circuitry 80 of external device 12. Impedance measurement circuitry 60 is, in the example described with reference to FIG. 3, shown in conjunction with sensing circuitry 52 of IMD 10. Similar to processing circuitry 50, 80, 98 and other circuitry described herein, impedance measurement circuitry 60 may be embodied as one or more hardware modules, software modules, firmware modules, or any combination thereof. Impedance measurement circuitry 60 may analyze impedance measurement data on a periodic basis to identify a decrease in subcutaneous impedance in patient 4 and alert patient 4 when the decrease indicates onset of a possible heart failure decompensation event.

In some examples, impedance measurement circuitry 60 may measure current or impedance values additional to impedance values previously determined, in response to receiving a signal from one or more other medical devices (e.g., via communication circuitry 54). In some examples, the one or more other medical devices may include a sensor device, such as an activity sensor, heart rate sensor, a wearable device worn by patient 4, a temperature sensor, etc. That is, the one or more other medical devices may, in some examples, be external to IMD 10. In such examples, the other medical devices may interface with IMD 10 via communication circuitry 54.

In some examples, IMD 10 may include the one or more other medical devices, such as by having the other medical devices included within housing 15 or otherwise fixed to an inner or outer portion of IMD 10. For example, the other medical device may include one or more of sensors affixed to an inner or outer portion of IMD 10. In any event, processing circuitry 50 may receive one or more signals from one or more medical devices that trigger processing circuitry 50 to control impedance measurement circuitry 60 to perform impedance measurements. In this way, processing circuitry 50 may determine current impedance values (e.g., a daily average), or impedance values additional to impedance values previously determined, in response to receiving one or more signals from another medical device, such as a sensor device.

For example, impedance measurement circuitry 60 may determine a received signal includes a trigger that causes impedance measurement circuitry 60 to measure one or more impedance values using electrodes 16. In a non-limiting example, impedance measurement circuitry 60 may receive signals indicating when patient 4 has low activity. In response to receiving the signal indicating an activity level, impedance measurement circuitry 60 may measure one or more impedance values using electrodes 16. In another example, impedance measurement circuitry 60 may receive signals indicating when patient 4 has lower or higher heart rate compared to that of a heart rate threshold or signals indicating when patient 4 has a temperature that has become too low or too high compared to that of certain temperature thresholds, etc. In any event, impedance measurement circuitry 60 may determine whether the received signals includes triggering information that communicates to impedance measurement circuitry 60 that impedance measurement circuitry 60 is to perform physiological parameter measurements using electrodes 16.

In some examples, processing circuitry 50 may determine whether a combination of one or more signals received from one or more transmitting devices contains triggering information. Processing circuitry 50 may determine one or more signals individually include triggering information. In some examples, processing circuitry 50 may determine one or more signals in combination include triggering information. In response to determining the occurrence of triggering information, processing circuitry 50 may cause impedance measurement circuitry 60 to measure one or more impedance values using electrodes 16. In some examples, processing circuitry 50 may additionally use timing information. For example, processing circuitry 50 may start a timer based on the triggering information. In some examples, processing circuitry 50 may cause impedance measurement circuitry 60 to measure impedance values in accordance with a timing constraint (e.g., only perform measurements at night) following a triggering event, regardless of when the triggering event occurred during the day. In any event, processing circuitry 60 may cause IMD 10 to determine one or more tissue impedance values in response to the triggering event, such as in response to receiving a signal from a sensor device, where in some instances, IMD 10 may include the sensor device or the sensor device may be independent of IMD 10.

In some examples, impedance measurement circuitry 60 may measure impedance values on a periodic basis, such as on an hourly basis, daily basis, weekly basis, or the like. In one example, impedance measurement circuitry 60 may measure impedance values during a particular portion of a day. As an example, impedance measurement circuitry 60 may measure impedance values every twenty minutes for a predetermined number of hours, such as between noon and 5 pm. Processing circuitry 50 may determine a final measured impedance value by calculating an average of the measurements. In this case, the daily value may be the average of the impedances measured by impedance measurement circuitry 60 during the day (e.g., within a 24-hr time period, within a 24-hr time period where measurements are selectively taken between particular times and/or in response to certain triggers, etc.).

The final value may then be stored as a measured impedance value in storage device 56. For example, the measured impedance values may include the final averaged impedance value. In some examples, the impedance values may be stored in a buffer of impedance values, where the buffer is configured to store a number of impedance values that are used for calculating a final averaged value. Measured impedance values may also include a buffer of a plurality of past final averaged values. That is, measured impedance values may include a buffer of past daily measured impedance values.

In some examples, impedance measurement circuitry 60 may be configured to sample impedance measurements at a particular sampling rate. In such examples, impedance measurement circuitry 60 may be configured to perform downsampling of the received impedance measurements. For example, impedance measurement circuitry 60 may perform downsampling in order to decrease the throughput rate or to decrease the amount of data transmitted to processing circuitry 50. This may be particularly advantageous where impedance measurement circuitry 60 has a high sampling rate when active.

In some examples, processing circuitry 50 may perform an impedance measurement by causing impedance measurement circuitry 60 (via switching circuitry 58) to deliver a voltage pulse between at least two electrodes 16 and examining resulting current amplitude value measured by impedance measurement circuitry 60. In some examples, switching circuitry 58 delivers signals that do deliver stimulation therapy to the heart of patient 4. In other examples, these signals may be delivered during a refractory period, in which case they may not stimulate the heart of patient 4.

In other examples, processing circuitry 50 may perform an impedance measurement by causing impedance measurement circuitry 60 (via switching circuitry 58) to deliver a current pulse across at least two selected electrodes 16. Impedance measurement circuitry 60 holds a measured voltage amplitude value. Processing circuitry 50 determines an impedance value based upon the amplitude of the current pulse and the amplitude of the resulting voltage that is measured by impedance measurement circuitry 60. IMD 10 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue, subcutaneous tissue, or muscle tissue.

In certain cases, IMD 10 may measure subcutaneous impedance values that include both a resistive component and a reactive component (e.g., X, XL, XC), such as in an impedance triangle. In such cases, IMD 10 may measure subcutaneous impedance during delivery of a sinusoidal or other time varying signal by impedance measurement circuitry 60, for example. Thus, as used herein, the term "impedance" is used in a broad sense to indicate any collected, measured, and/or calculated value that may include one or both of resistive and reactive components. In some examples, subcutaneous tissue impedance values are derived from subcutaneous tissue impedance signals received from electrodes 16.

In the example illustrated in FIG. 3, processing circuitry 50 is capable of performing the various techniques described in FIGS. 6-9. To avoid confusion, processing circuitry 50 is described as performing the various impedance processing techniques proscribed to IMD 10, but it should be understood that these techniques may also be performed by other processing circuitry (e.g., processing circuitry 80 of external device 12, etc.).

In various examples, processing circuitry 50 may perform one, all, or any combination of the plurality of impedance scoring techniques discussed herein. In performing the scoring techniques, IMD 10 may generate an alert upon determining that a decrease in impedance indicates that patient 4 is likely to experience a heart failure decompensation event. For example, IMD 10 may provide an audible or tactile alert in the form of a beeping noise or a vibrational pattern. Alternatively, IMD 10 may send an alert signal to external device 12 that causes external device 12 to provide an alert to patient 4. External device 12 may provide an audible, visual, or tactile alert to patient 4. Once patient 4 is alerted, patient 4 may then seek medical attention, e.g., by checking into a hospital or clinic. The alerts may be separated into various degrees of seriousness as indicated by an impedance score.

Sensing circuitry 52 may also provide one or more impedance signals to processing circuitry 50 for analysis, e.g., for analysis to determine impedance scores according to the techniques of this disclosure. In some examples, processing circuitry 50 may store the impedance values, impedance score factors (e.g., fluid indices, average impedance values, reference impedance values, buffer values, etc.), and impedance scores in storage device 56. Processing circuitry 50 of IMD 10, and/or processing circuitry of another device that retrieves data from IMD 10, may analyze the impedance values to determine a cardiac condition of patient 4 according to the techniques of this disclosure.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network.

Antenna 26 and communication circuitry 54 may be configured to transmit and/or receive signals via inductive coupling, electromagnetic coupling, near-field communications, RF communication, Bluetooth®, WI-FI™, or other proprietary or non-proprietary wireless communication schemes. In some examples, processing circuitry 50 may provide data to be uplinked to external device 12 via communication circuitry 54 and control signals using an address/data bus. In another example, communication circuitry 54 may provide received data to processing circuitry 50 via a multiplexer.

In some examples, processing circuitry 50 may send impedance data to external device 12 via communication circuitry 54. For example, IMD 10 may send external device 12 collected impedance measurements which are then analyzed by external device 12. In such examples, external device 12 performs the described processing techniques. Alternatively, IMD 10 may perform the processing techniques and transmit the processed impedance data to external device 12 for reporting purposes, e.g., for providing an alert to patient 4 or another user.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media. For example, storage device 56 may include random access memory (RAM), read-only memory (ROM), non-volatile RAM (NVRAM), electrically-erasable programmable ROM (EEPROM), erasable programmable ROM (EPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include impedance values and/or digitized cardiac EGMs, as examples.

The various components of IMD 10 are coupled to power source 91, which may include a rechargeable or non-rechargeable battery. A non-rechargeable battery may be capable of holding a charge for several years, while a rechargeable battery may be inductively charged from an external device, such as external device 12, on a daily, weekly, or annual basis, for example.

Figure 4:
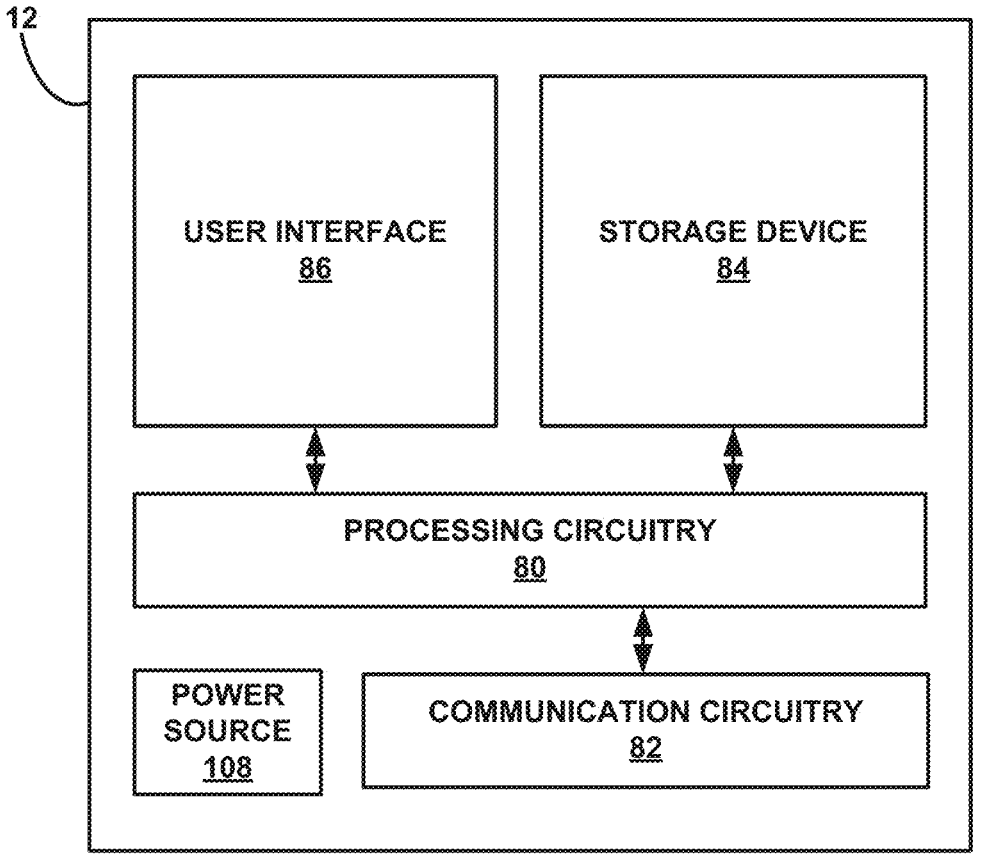
FIG. 4 is a functional block diagram illustrating an example configuration of the external device of FIG. 1, in accordance with one or more techniques disclosed herein.

FIG. 4 is a block diagram illustrating an example configuration of components of external device 12. In the example described with reference to FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, NFC technologies, RF communication, Bluetooth®, WI-FI™, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution. Storage device 84 may also store historical impedance data, timing information (e.g., number of days since implantation of the IMD, number of days since the fluid index has been above a certain threshold, etc.).

Data exchanged between external device 12 and IMD 10 may include operational parameters (e.g., resolution parameters). External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., impedance data, fluid index values, and/or impedance scores) to external device 12. In turn, external device 12 may receive the collected data from IMD 10 and store the collected data in storage device 84. Processing circuitry 80 may implement any of the techniques described herein to analyze impedance values received from IMD 10, e.g., to determine fluid index values, impedance scores, etc. Using the impedance analysis techniques disclosed herein, processing circuitry 80 may then determine a heart condition status of patient 4 and/or generate an alert based on the heart condition status.

A user, such as a clinician or patient 4, may interact with external device 12 through user interface 86. User interface 86 includes a display (not shown), such as an LCD or an LED display or other type of screen, with which processing circuitry 80 may present information related to IMD 10, e.g., cardiac EGMs, indications of detections of impedance changes, and quantifications of impedance changes, such as a quantification of impedance scores or fluid indices. In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Power source 108 delivers operating power to the components of external device 12. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 12. In other embodiments, traditional batteries (e.g., nickel cadmium or lithium ion batteries) may be used. In addition, external device 12 may be directly coupled to an alternating current outlet to power external device 12. Power source 108 may include circuitry to monitor power remaining within a battery. In this manner, user interface 86 may provide a current battery level indicator or low battery level indicator when the battery needs to be replaced or recharged. In some cases, power source 108 may be capable of estimating the remaining time of operation using the current battery.

Figure 5:
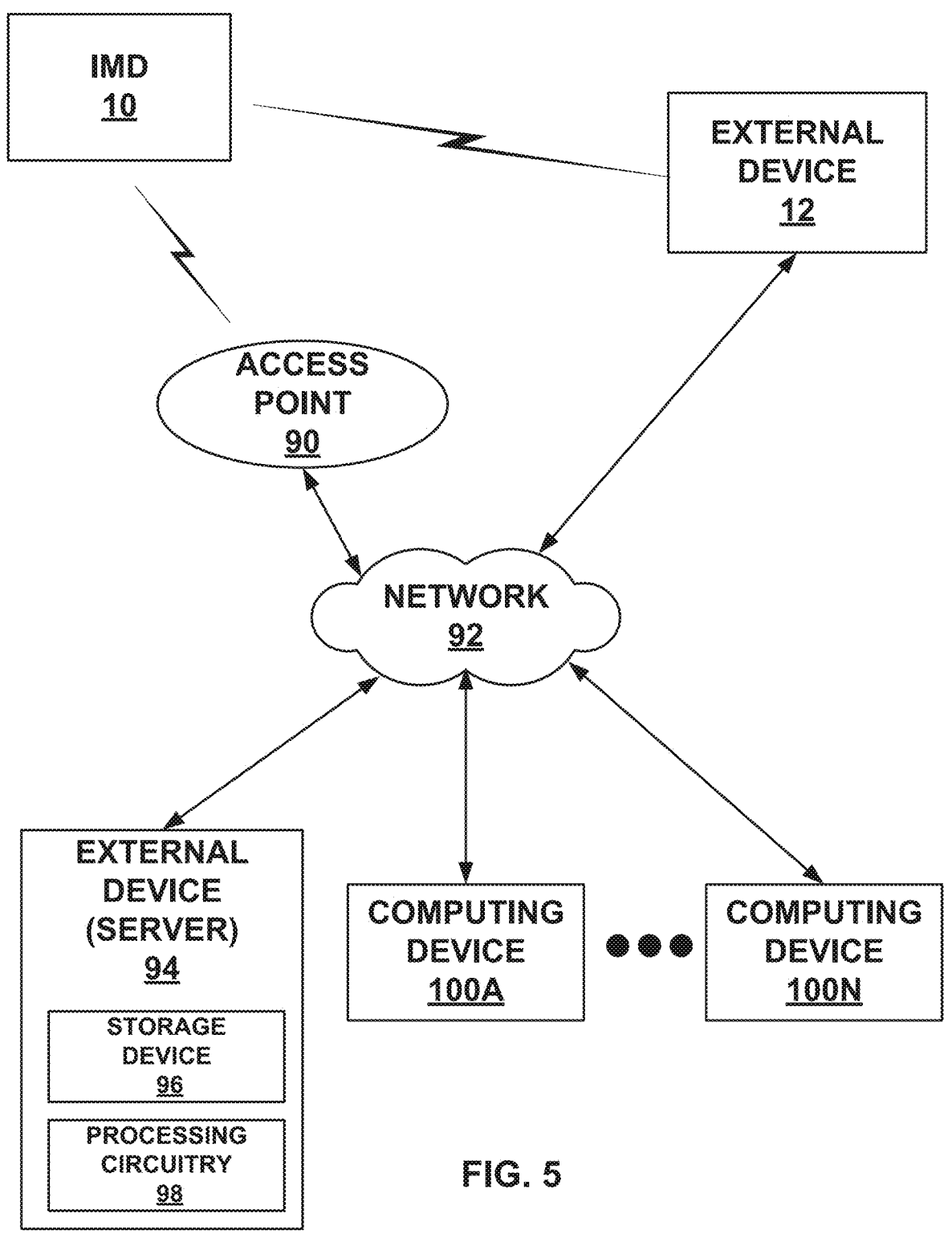
FIG. 5 is a block diagram illustrating an example system that includes an access point, a network, external computing devices, such as a server, and one or more other computing devices, which may be coupled to the IMD and external devices of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92. Network 92 may include a local area network, wide area network, or global network, such as the Internet. The system of FIG. 5 may be implemented, in some aspects, with general network technology and functionality similar to that provided by the Medtronic Care-Link® Network.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as impedance value information, impedance scores, and/or cardiac electrograms (EGMs), to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, server 94 may monitor impedance, e.g., based on measured impedance information received from IMD 10 and/or external device 12 via network 92, to detect worsening heart failure of patient 4 using any of the techniques described herein. Server 94 may provide alerts relating to worsening heart failure of patient 4 via network 92 to patient 4 via access point 90, or to one or more clinicians via computing devices 100. In examples such as those described above in which IMD 10 and/or external device 12 monitor the impedance, server 94 may receive an alert from IMD 10 or external device 12 via network 92, and provide alerts to one or more clinicians via computing devices 100. In some examples, server 94 may generate web-pages to provide alerts and information regarding the impedance, and may include a memory to store alerts and diagnostic or physiological parameter information for a plurality of patients.

In some examples, one or more of computing devices 100 may be a tablet or other smart device located with a clinician, by which the clinician may program, receive alerts from, and/or interrogate IMD 10. For example, the clinician may access data collected by IMD 10 through a computing device 100, such as when patient 4 is in between clinician visits, to check on a status of a medical condition. In some examples, the clinician may enter instructions for a medical intervention for patient 4 into an application executed by computing device 100, such as based on a status of a patient condition determined by IMD 10, external device 12, server 94, or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze impedance values received from IMD 10, e.g., to determine a heart condition status of patient 4 (e.g., worsening heart failure).

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

FIG. 6 is a flow diagram illustrating an example method for determining a heart condition status of patient 4 using reference impedance values, fluid index values, and impedance scores, in accordance with one or more techniques of this disclosure. Although described as being performed by IMD 10, the example method of FIG. 6 may be performed by any one or more of IMD 10, external device 12, or server 94, e.g., by the processing circuitry of any one or more of these devices.

In some examples, processing circuitry, e.g., processing circuitry 50 of IMD 10, processing circuitry 80 of external device 12, or processing circuitry 98 of server 94, may use absolute impedance values and statistical representations of impedance values when determining impedance scores. In some examples, absolute impedance values may generally refer to average impedance values.

In some examples, processing circuitry 50 may determine whether the fluid index values and statistical representations of impedance values satisfy respective thresholds. As discussed herein, the thresholds may include adaptive thresholds. For example, processing circuitry 50 may compare the fluid index values to an adaptive threshold. In some examples, an adaptive threshold is determined based on the intra-day variation in impedance values and the absolute impedance. In any event, processing circuitry 50 may determine an impedance score that indicates a heart condition status of patient 4.

In some examples, processing circuitry 50 may trigger a fluid index alert on a day that the fluid index is greater than or equal to a threshold, such as the adaptive threshold or a fixed, previously defined threshold or user-chosen threshold. In such examples, the fluid index alert may stop when the current fluid index value decreases below one half the threshold value. In this way, the fluid index value, after triggering the fluid index alert, may hover around the threshold without resetting the fluid index alert.

With reference to FIG. 6, processing circuitry 50 may determine first impedance values based on subcutaneous tissue impedance signals (110). The IMD 10 may be implanted in subcutaneous space 22 of patient 4. For example, IMD 10 may be implanted in interstitium 28, as shown in FIG. 2, and the subcutaneous tissue impedance signals may indicate the degree of fluid in the interstitium. In some examples, processing circuitry 50 may detect subcutaneous tissue impedance signals via electrodes 16. In some examples, only one of electrodes 16 is within subcutaneous space 22, with at least one other of electrodes 16 being within another layer of patient 4. In either case, processing circuitry 50 may determine, based at least in part on the subcutaneous tissue impedance signals, at least one first tissue impedance value that corresponds to a first time period.

The first impedance values may include historical impedance values received over a period of time. For example, processing circuitry 50 may receive first impedance values over 10 days, 13 days, 30 days, or any number of days. In some instances, processing circuitry 50 may receive at least one first impedance value(s) starting from the day of implantation. In other examples, processing circuitry 50 may collect but discard impedance values from being included as first impedance values until a certain number of days following implantation. For example, processing circuitry 50 may impose a delay of a predetermined number of days, such as 10 days, 13 days, 30 days, etc., before determining first impedance values. In some examples, the delay may only affect when processing circuitry 50 estimates a first reference value of a plurality of reference values, where reference values are discussed herein.

In some examples, the first impedance values may include raw signal data received from electrodes 16, which may be conditioned and processed using signal processing techniques before being stored. As would be understood by persons of skill in the art, impedance values are commonly described in units of ohms. In some examples, processing circuitry 50 may store the first impedance values to storage device 56. In some examples, processing circuitry 50 may transmit the first impedance values via communication circuitry 54. For example, processing circuitry 50 may transmit the first impedance values to external device 12. External device 12 may store the first impedance values to storage device 84. In such examples, processing circuitry 80 may determine an impedance score of patient 4 or may transmit or relay the data, via communication circuitry 82, to server 94, where server 94 may determine the impedance score of patient 4. Thus, although many of the techniques described herein are described as being performed by IMD 10, the methods may be performed, all or in part, by any one or more of IMD 10, external device 12, or server 94, e.g., by the processing circuitry of any one or more of these devices.

Processing circuitry 50 may also determine second impedance values based on subcutaneous tissue impedance signals (112). The second impedance values may correspond to a second period of time that is different from a period of time corresponding to the first impedance values. For example, the first and second time periods may be offset from one another. In some examples, the first and second time periods may overlap, whereas in other examples, the time periods and by extension, the impedance values, may be mutually exclusive of one another. In a non-limiting example, one or more of the second impedance values may be determined from the pool of first impedance values. For example, the second impedance values may correspond to impedance values measured during the first time period, in which the second impedance values correspond to a second time period that falls within the first time period. For example, the second impedance values may correspond to a daily impedance value of a current day, where the first time period includes values relating to the current day and days leading up to the current day. In this way, the first impedance values may correspond to a short-term mean that includes one or more impedance values, in addition to at least some of the second impedance values.

In some instances, processing circuitry, e.g., processing circuitry 50 of IMD 10, processing circuitry 80 of external device 12, or processing circuitry 98 of server 94, may incorporate the second impedance values in determining the first impedance values, where the second impedance values correspond to a current tissue impedance of patient 4 and the first impedance values correspond to historical impedance values that either include or do not include the current tissue impedance values (e.g., the second impedance values). For example, the at least one first tissue impedance value may include a plurality of historical tissue impedance values. As such, processing circuitry 50 may determine, based at least in part on the one or more subcutaneous tissue impedance signals, at least one second tissue impedance value that corresponds to a second time period different from the first time period (e.g., offset from the first time period). Processing circuitry, e.g., processing circuitry 50 of IMD 10, processing circuitry 80 of external device 12, or processing circuitry 98 of server 94, may store and/or transmit the second impedance values for subsequent analysis, as with the first impedance values.

In some examples, processing circuitry 50 may determine the second impedance values as a short-term mean (or other average) impedance value. The short-term mean may be the mean or weighted mean of the current impedance values from a plurality of days or hours (e.g., the last 12 hours, the last one day, two, three or four days, etc.). To determine the current and mean impedances, processing circuitry 50 may employ the techniques described in U.S. application Ser. No. 10/727,008 by Stadler et al., entitled "METHOD AND APPARATUS FOR DETECTING CHANGE IN INTRATHORACIC IMPEDANCE," filed on Dec. 3, 2003, and incorporated herein by reference in its entirety. In some examples, processing circuitry 50 may perform an average of impedance values over multiple cardiac cycles. In this way, processing circuitry 50 may obtain a less noisy signal and/or filter on respiration (AC component of signal) to obtain impedance (DC component of signal).

In some examples, processing circuitry, e.g., processing circuitry 50 of IMD 10, processing circuitry 80 of external device 12, or processing circuitry 98 of server 94, may identify the occurrence of missing subcutaneous impedance measurement data (e.g., the occurrence of corrupt data, gaps in data series, etc.). For example, processing circuitry 80 may identify the occurrence of missing data. In some examples, processing circuitry 80 may identify the occurrence of missing data, such as when unable to access certain data from an expected storage location of storage device 84 or when a missed transmission has occurred. In another example, processing circuitry 80 may determine that a data series includes a data gap indicating the occurrence of missing data (e.g., corrupt data). Processing circuitry 80 may identify the data gap, for example, based on a known transmission rate. In one example, IMD 10 may transmit impedance values to processing circuitry 80 on a periodic basis (e.g., daily). In such examples, processing circuitry 80 may determine the occurrence of missing data based on data missing for a particular timeframe, where impedance data is available preceding and/or following the particular timeframe. In another example, processing circuitry 80 may determine that certain data is corrupt or that the data contains outlier data that may indicate a transmission error or error in obtaining the data. In any event, processing circuitry 80 may transmit a request to IMD 10 for the missing data or may simply notify IMD 10 of the identified discrepancy.

Missing data may occur for any number of different reasons, such as a failed data transmission or if IMD 10 is unavailable at the time to perform impedance measurements for a particular measurement cycle. For example, IMD 10 may be unavailable to perform certain impedance measurements due to processing circuitry 50 responding to competing measurement requests. In one example, processing circuitry 50 may be responding to a higher priority measurement request, such as an ECG request under certain circumstances, in which sensing circuitry 52 may be unable to perform impedance measurements as expected.

In one example involving missing data, processing circuitry 80 or processing circuitry 98 may determine that one or more impedance values were expected to be received from IMD 10, but that the one or more impedance values were not received from IMD 10. In some examples, processing circuitry 80 or processing circuitry 98 may determine that one or more impedance values were not received from IMD 10, such as by detecting one or more dropped packets or by identifying gaps in data received from IMD 10. In some examples, external device 12 or server 94 may determine inconsistencies in data indicating corrupt, misleading, or otherwise discrepant data. For example, external device 12 may compare data received from IMD 10 to data received from other devices to determine whether the data is aligned or in agreement. In examples where external device 12 or server 94 identifies missing data, external device 12 or server 94 may transmit a notification to IMD 10 (e.g., via communication circuitry 54) identifying the discrepancy or otherwise indicating the occurrence of missing data. In response, processing circuitry 80 may attempt to correct for the discrepancy, for example, by identifying a cause of the missing data and/or attempting to alter IMD 10 to avoid losing data in the future.

In some examples, upon identifying the occurrence of one or more missing impedance values, processing circuitry, e.g., processing circuitry 50 of IMD 10, processing circuitry 80 of external device 12, or processing circuitry 98 of server 94, may be configured to interpolate or extrapolate data from one or more known tissue impedance values. For example, processing circuitry 80 may interpolate or extrapolate from known data points in order to complete a data series of impedance values measured over time. In some examples, processing circuitry 80 may interpolate or extrapolate upon identifying the occurrence of corrupt data and/or outlier data points. Although described as being performed by processing circuitry 80, the techniques of this disclosure are not so limited, and these techniques, among other techniques of this disclosure, may be performed by any one or more of IMD 10, external device 12, or server 94, e.g., by the processing circuitry of any one or more of these devices.

In some instances, processing circuitry 80 may include the interpolated or extrapolated data as part of the one or more tissue impedance values that are used to determine impedance scores. That is, processing circuitry 80 may attempt to complete a data series of impedance measurements using various interpolation or extrapolation techniques to cover the missing gaps in data. In some examples, processing circuitry 80 may use weighted averages for data corresponding to days having valid impedance measurement data. Processing circuitry 80 may use the weighted average data and the interpolated or extrapolated data to determine the fluid index.

In some examples, processing circuitry 80 may identify a fluid index reset condition that causes a fluid index value to reset to a baseline value based on an identification of missing data. In an illustrative example, processing circuitry 80 may determine that the number of days with missing impedance data (e.g., daily impedance average, etc.) is less than X number of days. In such instances, processing circuitry 80 may perform interpolation or extrapolation techniques as discussed above. If, however, processing circuitry 80 determines the number of days with missing impedance data satisfies a missing data threshold (e.g., 7 days of missing data, 14 days of missing data, etc.), then processing circuitry 80 may automatically cause the reference impedance value to reset, such that the reference impedance value recommences at an initial value, which results in the fluid index value being reinitialized to zero (or some other user-defined or fixed and previously defined baseline value). In some examples, processing circuitry 80 may reset the fluid index value to a baseline value of zero. In such examples, processing circuitry 80 may restart the fluid index computation starting from the baseline value. That is, the baseline value for the fluid index reset conditions may have a value of zero in some cases.

Although described as being performed by external device 12, techniques involving fluid index resets and missing data determinations may be performed by any one or more of IMD 10, external device 12, or server 94, e.g., by the processing circuitry of any one or more of these devices. For example, server 94 may determine the occurrence of missing data, corrupt data, or outlier data. In such examples, server 94 may perform the interpolation or extrapolation techniques in an attempt to complete the data series or otherwise, reset a fluid index value when too much data is missing or corrupt. As such, server 94 may communicate to external device 12 or IMD 10 that a fluid index reset condition has occurred or in cases where server 94 performs the techniques of this disclosure, such as determining the impedance score, server 94 may reset the fluid index and determine the impedance score using a baseline fluid index value.

In some examples, processing circuitry, e.g., processing circuitry 50 of IMD 10, processing circuitry 80 of external device 12, or processing circuitry 98 of server 94, may determine reference impedance value(s) based on the first impedance values (114). For example, processing circuitry 50 of IMD 10 may determine, based at least in part on the at least one first tissue impedance value, one or more reference impedance values. The reference impedance values may provide a statistical representation of values based on the first impedance values. For example, in determining the one or more reference impedance values, processing circuitry 50 may determine a statistical representation of at least one first tissue impedance value correspond to the first time period. In determining the statistical representation of the at least one first tissue impedance value, the processing circuitry 50 may determine an average, a mode, a median, a range, a regression model, or a standard deviation in order to represent the at least one first tissue impedance value. Reference impedance value(s) are discussed in further detail with reference to FIG. 9.

When calculating reference impedance values, processing circuitry 50 may adjust slope values of a reference value to a next reference value to accommodate for the rapid rise of impedance in the first few months (e.g., drift-up and drift-down parameters). In some examples, processing circuitry 50 may adaptively calculate reference impedance values over time. For example, processing circuitry 50 may adjust drift-up and drift-down parameters in a piece-wise linear fashion to accommodate for the rapid rise of impedance in the first few months. As such, processing circuitry 50 may calculate reference impedance in a manner that accommodates the different rates of change in impedance over time. In other words, reference impedance values may be calculated differently during different periods of time. For example, the reference impedance values may be calculated to allow for a greater change in reference impedance during day 34 to day 60 following implantation or system modification than during days 61 to 120. The reference impedance values may then be calculated to allow for a lesser change in value for the days extending past day 120 than for the previous time period.

For example, processing circuitry 50 may adjust the reference slope values by adjusting drift-up and drift-down parameters that are scaled from nominal drift values (e.g., drift-up nominal and drift-down nominal). In some examples, the nominal drift value for the drift-up reference may be 0.18 ohms per day. In another example, the nominal drift value for the drift-down reference may be 0.05 ohms per day. In examples where the fluid index calculation starts on day 34 after implant, processing circuitry 50 may calculate the drift-up parameter from day 34 to day 60 as a nominal drift-up value scaled by a predetermined multiplier. In some examples, the predetermined multiplier from day 34 to day 60 may be between 9 and 11 (e.g., 10). In other examples, the predetermined multiplier from day 34 to day 60 may be less than or greater than 10.0. For example, the predetermined multiplier from day 34 to day 60 may be 3.5.

In some examples, processing circuitry 50 may calculate the drift-down reference parameter as a nominal drift-down value scaled by a predetermined multiplier. In some examples, the predetermined multiplier from day 34 to day 60 may be a negative fractional value (e.g., negative 0.01). In other examples, the predetermined multiplier may be a positive fractional value (e.g., positive 0.25).

From day 61 to day 120, processing circuitry 50 may calculate the drift-up parameter as the nominal drift-up value scaled by a different multiplier. For example, the drift-up multiplier for day 61 to day 120 may be a positive fractional value (e.g., positive 2.5). In certain examples, the drift-up parameter for day 61 to day 120 may be 0.45, which is a nominal value of 0.18 multiplied by 2.5, for example. From day 61 to day 120, the drift down multiplier may be a positive fractional value (e.g., positive 0.5), which would result in a drift down parameter of 0.025. In some examples, the cutoff point for number of days may differ. For example, the cutoff may be day 61 to day 100 in some examples, instead of day 120, where day 120 is used as a benchmark for only certain examples. In any event, processing circuitry 50 may utilize a first drift-up parameter and a first drift-down parameter in the first 60 days of implant when determining reference impedance values in the first 60 days and may utilize a second drift-up parameter and a second drift-down parameter in the first 100 or 120 days of implant when determining reference impedance values in the first 100 or 120 days of implant.

As such, processing circuitry 50 may identify a first fluid index calculation to determine at least a first subset of the one or more fluid index values and identify a second fluid index calculation to determine at least a second subset of the one or more fluid index values. As described above, the identification of which calculation to use is based at least in part on the number of days the fluid index value has been greater than zero. As such, day 61, for this fluid index calculation, indicates that the fluid index value has been greater than zero for 61 days.

Although described below as being performed by processing circuitry 50, these techniques may be performed by any one or more of IMD 10, external device 12, or server 94, e.g., by the processing circuitry of any one or more of these devices. In some examples, processing circuitry, e.g., processing circuitry 50 of IMD 10, processing circuitry 80 of external device 12, or processing circuitry 98 of server 94, may determine reference impedance values in accordance with the techniques described in U.S. application Ser. Nos. 12/184,149 and 12/184,003 by Sarkar et al., entitled "USING MULTIPLE DIAGNOSTIC PARAMETERS FOR PREDICTING HEART FAILURE EVENTS," and "DETECTING WORSENING HEART FAILURE BASED ON IMPEDANCE MEASUREMENTS," both filed on Jul. 31, 2008, and both of which are incorporated herein by reference in their entirety.

Figure 9:
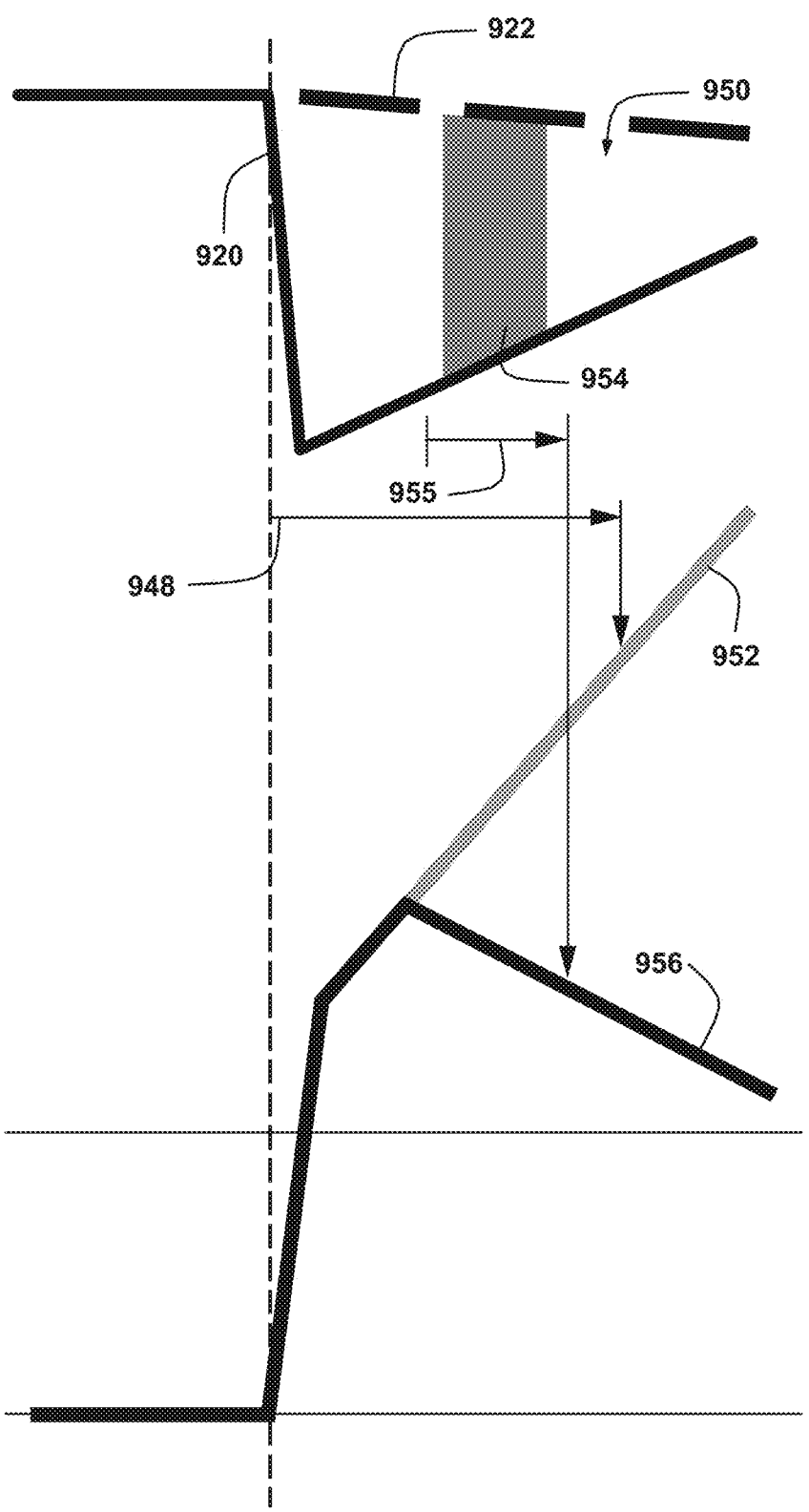
FIG. 9 is an example timing diagram illustrating use of a finite buffer to limit accumulation of a fluid index over time, in accordance with one or more techniques disclosed herein.

With reference still to FIG. 6, processing circuitry, e.g., processing circuitry 50 of IMD 10, processing circuitry 80 of external device 12, or processing circuitry 98 of server 94, may compare the second impedance values to the reference impedance value(s) (116). For example, processing circuitry 50 may utilize a comparator to determine whether the second impedance values are greater than, less than or equal to the reference impedance value(s). An example visual depiction of the comparison of impedance values is illustrated in FIG. 9, discussed in further detail below. In some examples, processing circuitry 50 may determine a difference between the reference value(s) and second impedance values. In examples where the second impedance values represent the daily average value, processing circuitry 50 may compare the daily average value to the reference value.

In some examples, processing circuitry 50 may identify a resolution parameter for determining at least one of: the first tissue impedance value(s), the reference impedance value (s), and the second tissue impedance value(s). For example, processing circuitry 50 may identify the resolution parameter for impedance measurements as specifying that IMD 10 perform impedance measurements every hour or in other examples, processing circuitry 50 may average impedance measurements performed over a day into a single impedance measurement. In some examples, the resolution parameter may include a filter that is based on a time constraint or on an activity level.

For example, processing circuitry 50 may derive a single daily impedance measurement from only daytime measurements or only nighttime measurements or impedance measurements performed for a sub-time period during a 24-hour period. Also, processing circuitry 50 may only use impedance measurements captured during periods of low activity to calculate overall daily measurements. In some examples, processing circuitry, e.g., processing circuitry 50 of IMD 10, processing circuitry 80 of external device 12, or processing circuitry 98 of server 94, may exclude, based on the resolution parameter or the corresponding filter, a subset of tissue impedance signals from the subcutaneous tissue impedance signals when determining the first or second tissue impedance values.

In some examples, processing circuitry, e.g., processing circuitry 50 of IMD 10, processing circuitry 80 of external device 12, or processing circuitry 98 of server 94, may determine one or more sub-time periods that correspond to the first time period or the second time period. For example, processing circuitry 50 may identify the resolution parameter as specifying a 10 second measurement every hour. In other examples, processing circuitry 50 may identify the resolution parameter as specifying measurements during periods of low activity count, where all hourly measurements with low activity counts being averaged to determine a daily impedance value over a 24-hour period. As such, processing circuitry 50 may apply a filter to the subcutaneous tissue impedance signals in accordance with the sub-time periods specified by the filter. It should be noted that although described as being performed by processing circuitry 50, the resolution parameter and filtration techniques may be performed by any one or more of IMD 10, external device 12, or server 94, e.g., by the processing circuitry of any one or more of these devices.

In some examples, body position of patient 4 may alter impedance measurements. For example, electrodes 16 may migrate within subcutaneous space 22 when patient 4 changes positions. In such examples, processing circuitry 50 may use a resolution parameter or filter to reject impedance values associated with changes in impedance that occur due to the change in body position of patient 4. In some examples, processing circuitry 50 may ignore or reject certain subcutaneous tissue impedance signals based on a particular change in body position. In another example, processing circuitry 50 may reset the reference impedance to be based on the new body position. In any event, the body position filter may be programmable by a user, such as a physician. For example, processing circuitry 50 may receive body position filter parameters that indicate that an impedance score is to be based on subcutaneous tissue impedance values received during times when patient 4 is laying down or when patient 4 is upright, etc.

In some examples, processing circuitry 50 may determine not to categorize a heart or health status of patient 4 for a period of time based on the position of patient 4. For example, processing circuitry 50 may determine patient 4 is standing upright or is laying down and as such, may forego categorizing the health status of patient 4 during the time when patient 4 is in the particular position. In some examples, the particular position may be programmable by a user.

In some examples, the resolution parameter or filter may be based on processing circuitry 50 identifying an orientation of IMD 10. For example, processing circuitry 50 or impedance measurement circuitry 60 may be configured to obtain impedance measurements when patient 4 has a particular posture that causes IMD 10 to be oriented in a particular orientation. Processing circuitry 50 may use one of sensor(s) 62, such as a 3-axis accelerometer, in order to determine the orientation of IMD 10. In such examples, processing circuitry 50 may be configured to obtain impedance measurements when patient 4 is in the desired position. For example, processing circuitry 50 may be configured to obtain impedance measurements when patient 4 is lying down, such that accelerometer values of IMD 10 indicate that patient 4 is lying down.

In one example, processing circuitry, e.g., processing circuitry 50 of IMD 10, processing circuitry 80 of external device 12, or processing circuitry 98 of server 94, may identify one or more accelerometer values from one or more accelerometers corresponding to IMD 10 and/or another medical device, such as a wearable medical device having an accelerometer. In some instances, processing circuitry 50 may determine that an accelerometer value from the one or more accelerometer values satisfies an orientation threshold. For example, processing circuitry 50 may set an orientation threshold, such that the threshold is satisfied when the orientation of IMD 10 indicates that patient 4 is oriented upright, laying down, at an incline, face downward while laying, etc. For example, processing circuitry 50 may be initialized with IMD 10 in a particular orientation relative to an orientation of patient 4 and a reference plane, such as a ground plane. As such, accelerometer data may indicate an orientation of patient 4. In some examples, processing circuitry 50 may determine that relative changes in one or more accelerometer values indicates an orientation of patient 4 that satisfies the orientation threshold. As such, a single accelerometer value may be based on multiple accelerometer values so as to indicate relative changes in the orientation of IMD 10 and/or patient 4.

In some examples, processing circuitry 50 may determine that the accelerometer value satisfies the orientation threshold. In such examples, processing circuitry 50 may determine tissue impedance values based at least in part on the determination that the accelerometer value satisfies the orientation threshold. For example, processing circuitry 50 may control impedance measurement circuitry 60 to perform impedance measurements in response to determining that the accelerometer value indicates a desired orientation of patient 4 for performing impedance measurements.

In another example, processing circuitry 50 may be configured to impose a delay period between impedance measurements after processing circuitry 50 has detected that IMD 10 is in the proper orientation and/or that patient 4 is in the desired position. In a non-limiting example, processing circuitry 50 may impose a 30-minute delay or a one-hour delay after processing circuitry 50 detects that patient 4 is lying down, so as to allow time for the fluid of patient 4 to redistribute following the change in position.

In some examples, processing circuitry 50 may use filters or resolution parameters that have different night/day thresholds, different position thresholds, orientation thresholds, or different activity level thresholds. For example, processing circuitry 50 may ignore certain impedance measurements taken during a time when an activity level of patient 4 exceeds an activity level threshold, such as when processing circuitry 50 or another sensor device interfacing with IMD 10, indicates a particular activity level of patient 4. In another example, processing circuitry 50 may determine that IMD 10 satisfies a predefined orientation threshold. For example, the predefined orientation threshold may be based on an orientation indicating that patient 4 is in the desired position for impedance measurements. In response to IMD 10 satisfying the predefined orientation threshold, processing circuitry 50 may determine one or more tissue impedance values. For example, processing circuitry 50 may determine tissue impedance values by causing impedance measurement circuitry 60 to perform an impedance measurement.

Processing circuitry 50 of IMD 10, processing circuitry 80 of external device 12, or processing circuitry 98 of server 94 may then determine a fluid index of patient 4 based at least in part on the comparison (117). In some examples, IMD 10 may determine fluid index values in accordance with the techniques described in U.S. application Ser. Nos. 12/184,149 and 12/184,003 by Sarkar et al., entitled "USING MULTIPLE DIAGNOSTIC PARAMETERS FOR PREDICTING HEART FAILURE EVENTS," and "DETECTING WORSENING HEART FAILURE BASED ON IMPEDANCE MEASUREMENTS," both filed on Jul. 31, 2008, and both of which are incorporated herein by reference in their entirety. For example, as described and applicable throughout, IMD 10 may transmit various input data to external device 12 and/or server 94, where external device 12 and/or server 94 determine the fluid index of patient 4 on any given day. In such examples, external device 12 or server 94 may output the fluid index value, such as to a storage location (e.g., storage device 96) or back to IMD 10, such that processing circuitry 50 may store the fluid index values to storage device 56.

In some examples, at least three morphologies of impedance decreases have been found to occur in patients. The first form of impedance decrease represents a gradual and consistent decrease in impedance over an extended period of time. The duration of this type of impedance decrease is longer than a month. This impedance decrease is strongly associated with worsening cardiac heart failure.

The second form of impedance decrease is characterized by a sudden drop in impedance followed by a trend of increasing impedance back towards the baseline impedance. This type of event may result from changes in patient compliance behaviors, such as medication or dietary indiscretion, or result from acute decompensation that may lead to medical intervention. Thus, some of these crossing may be critical while others may be less critical.

The third form of impedance decrease results from small DC shifts in impedance. Because these small shifts may occur several times, they may eventually lead to threshold crossings if the fluid index is accumulated over a long period of time. For example, a sustained shift in impedance of even two or three ohms may result in a crossing if sustained for a sufficient period of time. The standard deviation of day-to-day variation in impedance has been observed to be on the order of three ohms. Thus, this class of decrease in impedance is not considered clinically critical but can lead to false alerts if the processing technique is not properly designed.

Moreover, the implant procedure causes another distinct feature in the impedance trend of the patient. This feature is that the daily impedance increases over several months following the implant procedure and the rate of increase over time slows as the daily impedance plateaus toward a baseline value. This phenomenon is believed to be due to the drying out of a device pocket and encapsulation of a lead after being implanted. In other words, because a device pocket is filled with fluid immediately following an implant procedure the measured impedance is relatively low because the resistance of the fluid is less than the resistance of body tissue. However, as the fluid dissipates over time the resistance increases and the rate at which the fluid dissipates decreases as time progresses. This can result in the daily impedance tending to be higher than the reference impedance during the first few months following the implant procedure. As a result, the fluid index may be less sensitive to actual decreases in the daily impedance. This is undesirable.

IMD 10, e.g., processing circuitry 50, may address these issues through adaptive processing techniques. The adaptive processing techniques may limit fluid index threshold crossings for small amplitude shifts in the measured impedance, limit fluid index increases while the daily impedance is recovering or increasing toward a baseline value and allow the rate of change of the reference impedance value to change over time.

In one example, processing circuitry 50 may calculate the fluid index based on the variability of measured impedance values. In particular, system 2 may determine the fluid index in a way that mitigates the accumulation of decreasing impedance when there is a greater variability on a day-to-day basis. Processing circuitry 50 may also give greater weight to the variability according to the time that has elapsed since implant or a prior detected event.

In an additional example processing circuitry 50 may calculate the fluid index by accumulating the fluid index over a finite period of time using a finite number of differences between measured and reference impedances. That is, system 2 may use a sliding window technique to calculate the fluid index. This technique may avoid accumulating the fluid index to an alert condition as the baseline impedance tries to "catch-up" to a baseline shift in the measured impedances.

In a further example, processing circuitry 50 may calculate the fluid index over time by factoring in a time dependent value. In this way the time dependent value may be used to increase the value of the fluid index after the measured impedances have been below the reference impedance for a threshold duration, e.g., a month, which may indicate a clinically significant worsening of patient condition.

As such, processing circuitry 50 may take into account the following considerations when determining fluid index values: variability, finite memory, duration, and as discussed above, reference slope adjustments. Variability considerations refer generally to IMD 10 accumulating fluid index values less in patients with higher day-to-day variability in impedance measurements. Finite memory considerations refer generally to IMD 10 accumulating fluid index values over a finite period of time instead of accumulating from the start of an impedance decline (e.g., a fluid index event) until the end of the fluid index event (e.g., when the second impedance values rise above the reference value). Duration considerations refer generally to IMD 10 accumulating impedance values when an impedance decline continues for a prolonged period of time. The techniques employed to account for these considerations in calculating a fluid index are discussed herein (e.g., with reference to FIG. 8). Although certain techniques herein are described as being performed by processing circuitry 50, these techniques may be performed by any one or more of IMD 10, external device 12, or server 94, e.g., by the processing circuitry of any one or more of these devices.

With reference still to FIG. 6, processing circuitry, e.g., processing circuitry 50 of IMD 10, processing circuitry 80 of external device 12, or processing circuitry 98 of server 94, may determine an impedance score using the fluid index value (118). For example, processing circuitry 50 may determine an impedance score from the absolute impedance value or from a daily average impedance value. In some examples, processing circuitry 50 calculates the fluid index value as the sum of differences between reference impedance values and daily impedance values. In some examples, the impedance score may be based on the daily average or the absolute impedance value. For example, where the fluid index value is zero on a given day, the impedance score may increment based on the absolute impedance value for the day or based on the daily average impedance value. In any event, processing circuitry 50 may use the absolute impedance (e.g., average impedance) to determine the impedance score and the fluid index value, where the fluid index for the day is a non-zero value.

In some examples, processing circuitry, e.g., processing circuitry 50 of IMD 10, processing circuitry 80 of external device 12, or processing circuitry 98 of server 94, may initialize the impedance score at an initial starting value. In some examples, processing circuitry 50 may set the initial starting value at a baseline value of zero (e.g., impedance score=0). In other examples, processing circuitry 50 may initialize the impedance score at a non-zero value. For example, processing circuitry 50 may receive a command from external server that the impedance score should initialize at a starting value of one so as to bias the impedance score. This may be done based on history of patient 4 or if the IMD 10 is a replacement for a previous IMD 10 that had already incremented the impedance score above zero.

In some examples, processing circuitry, e.g., processing circuitry 50 of IMD 10, processing circuitry 80 of external device 12, or processing circuitry 98 of server 94, may increment the impedance score based on triggering events that indicate a subcutaneous tissue impedance event of patient 4. In some examples, processing circuitry 50 may increment the impedance score by a first value in response to a first group of one or more triggering events. processing circuitry 50 may increment the impedance score by a second value in response to a second group of one or more triggering events. The first value, in some examples, may increment the impedance score by one point, whereas the second value, in some examples, may increment the impedance score by two points. Other point values may be used that are greater than or less than the first value or the second value. In some examples, processing circuitry 50 may detect multiple triggering events during a single iteration of the scoring cycle, in which case a sum of values may be applied to the impedance score. For example, processing circuitry 50 may increment the impedance score by four points when processing circuitry 50 determines that two triggering events are present, one triggering event corresponding to a two point incremental value and where another triggering event also corresponds to a two point incremental value. In some examples, processing circuitry 50 may determine a total impedance score between a value of 0 on the low end and 7 on the high end, as discussed below. The techniques for determining impedance scores are discussed herein (e.g., with reference to FIG. 7).

In some examples, processing circuitry 50 may decrement or reset the impedance score when certain other predefined conditions are met. In one example, processing circuitry 50 may determine that the subcutaneous impedance is higher than the reference impedance value. In such instances, processing circuitry 50 may determine the occurrence of a dry index event that is the opposite of a fluid index event. In some examples, processing circuitry 50 may determine a dry index value by accumulating the differences between subcutaneous impedance and the reference impedance value in cases where the subcutaneous impedance is higher than the reference impedance value. As such, higher dry index values may decrement the impedance score similar to how higher fluid index values may increment impedance scores, in accordance with one or more techniques disclosed herein.

In some examples, processing circuitry 50 may determine a heart condition status of patient 4 based on the impedance score (119). For example, processing circuitry 50 may periodically compare the impedance score to one or more risk thresholds. In some examples, processing circuitry 50 may perform a comparison of the impedance score to the risk thresholds at a same time each day (e.g., at the end of the day). In another example, processing circuitry 50 may determine a heart or health condition status of patient 4 at multiple intervals each day. In yet another example, processing circuitry 50 may determine the heart or health condition status of patient 4 at longer intervals, such as once a week or once every two weeks. The intervals may be determined based on certain cardiac risk factors of patient 4.

In some examples, processing circuitry, e.g., processing circuitry 50 of IMD 10, processing circuitry 80 of external device 12, or processing circuitry 98 of server 94, may determine a heart condition status as a heart failure risk status. For example, processing circuitry 50 may use risk status categories, such as low, medium, high, etc. In some examples, processing circuitry 50 may use a different number of risk categories, such as including a category for very high risk in some instances or very low risk. In addition, processing circuitry 50 may not include certain categories, such as the medium risk category, and instead only monitor low and high-risk categories. In some examples, processing circuitry 50 may compare the impedance score to risk thresholds to determine a heart condition status.

In a non-limiting example, processing circuitry, e.g., processing circuitry 50 of IMD 10, processing circuitry 80 of external device 12, or processing circuitry 98 of server 94, may use a different number of risk categories may determine risk levels as follows: low risk if the impedance score is 0, medium risk if the impedance score is greater than or equal to 1 but less than or equal to 6, and high if the impedance score is greater than or equal to 7. Risk thresholds may be set (e.g., programmably by a user) based on optimization considerations and may be based on the specific values used to determine the fluid index. For instance, various different constants may be used to determine the reference impedance values (e.g., different values for drift up and drift down parameters, etc.) that would cause a medium risk to correspond to an impedance score of between 1 and 5 or a high risk to correspond to an impedance score of greater than or equal to 6. In any case, IMD 10 will employ the same algorithmic techniques to determine fluid index values, impedance scores, and risk categories, irrespective of user-programmable constants. In some instances, a user may utilize a user interface to set the user-programmable constants. For example, a user may be able to set what impedance scores constitute high risk, medium risk, and low risk.

In another example, IMD 10 determine status levels for other health conditions, such as edema, preeclampsia, hypertension, etc., based on the impedance score. In such examples, IMD 10 may identify various risk thresholds for each health monitoring situation. For example, the risk thresholds for heart failure decompensation may be different from other heart-related conditions. In some instances, the number of risk categories may differ as well. For instance, IMD 10 may identify a high and a low risk level for preeclampsia that may correspond to variable risk thresholds that differ at various stages of a pregnancy, for example. In any event, the impedance score may indicate conditions that appear to alter impedance levels within subcutaneous space 22 prior to warranting medical intervention.

In one example, IMD 10 may utilize the impedance measurements to determine a respiration rate (RR) of patient 4. For example, the subcutaneous tissue impedance values may include low-frequency fluctuations that correspond to the RR. Subcutaneous impedance is sensitive to conductivity of fluid around electrodes 16. With each inhalation, the intrathoracic pressure reduces increasing pulmonary blood volume. An increase in pulmonary blood volume tends to lead to a reduction of pulmonary artery pressure. A reduction of pulmonary artery pressure tends to cause a reduction of right arterial pressure and an increase of venous return. This may cause a reduction of extracellular/extra-vascular volume and thus, an increase in impedance. The opposite sequence of events leads to reduction of impedance with exhalation. In another example, a movement of the chest wall of patient 4 may lead to changes in measured impedance, as well. In some examples, IMD 10 may determine respiration rate (RR) in accordance with U.S. application Ser. No. 16/450,250 by Sarkar et al., entitled "SENSING RESPIRATION PARAMETERS BASED ON AN IMPEDANCE SIGNAL," filed on Jun. 24, 2019, incorporated herein by reference in its entirety.

IMD 10 may use the impedance score to determine, on any given day, the subcutaneous impedance-based heart failure (HF) risk of patient 4. The risk categories may also indicate risk levels for various cardiac related ailments that may include subcategories of HF (e.g., heart valve failure, cardiac arrest, etc.) or other organ complications, such as lung, liver, or kidney failure.

Although described in terms of IMD 10 performing the techniques of FIGS. 6-9, it is to be understood that any number of different components of system 2, and combinations thereof, may perform the techniques disclosed. For example, IMD 10 may transmit raw impedance data to external device 12, where external device 12 may determine the first impedance values, second impedance values, reference impedance values, fluid index values, etc. In some example, external device 12 may include multiple computing devices (e.g., a remote cloud server) that collectively determines the heart condition status of patient 4. In addition, it is to be understood that the components of system 2 (e.g., processing circuitry 50, impedance measurement circuitry 60, processing circuitry 80, etc.) may perform some or all of the techniques of FIGS. 6-9 in parallel or in conjunction with one another.

It should be noted that the above techniques of FIG. 7 may also be performed on a periodic basis. For example, the health or heart condition status may be determined according to a resolution parameter setting of IMD 10 (e.g., the resolution parameter used to signal a frequency at which electrodes 16 should probe for impedance measurements). In other examples, the health or heart condition status may be calculated irrespective of the resolution parameter, which, for example, may apply to the fluid index determination, impedance score determination, impedance probing frequency, and/or the reference impedance value determination, but not the health or heart condition status determination. For instance, IMD 10 may calculate the health or heart condition status at several time intervals each day (e.g., once in the morning, once in the afternoon, once in the evening, once after meals, etc.). IMD 10 may calculate the health or heart condition status once a day, each week, every two weeks, each month, etc. In some examples, IMD 10 may also calculate the health or heart condition status in response to a user command (e.g., from a physician, from a user interface) or in response to a satisfaction of another condition, such as upon receiving or determining a new impedance score or a modification to an impedance score. IMD 10 may also trigger a health or heart condition status calculation when an activity level or other physiological parameter satisfies a threshold (e.g., low activity when patient 4 is resting or sleeping). In one other example, IMD 10 may determine the health or heart condition status of patient 4 on a per measurement basis, such as on a per fluid index determination basis or on a per impedance measurement basis. A person of skill in the art would appreciate that various periods may exist for when IMD 10 or external device 12 may determine a health or heart condition status in accordance with FIG. 6, transmit a health or heart condition status, receive a health or heart condition status, etc.

FIG. 7 is a flow diagram illustrating an example method for determining impedance scores. In some instances, processing circuitry 50 may determine the impedance score of patient 4. Processing circuitry 50 may periodically determine an impedance score at various intervals. In some examples, processing circuitry 50 may determine an impedance score in response to a user request for a current impedance score. In some examples, external device 12 may determine the impedance score of patient 4. For brevity, certain techniques are described with reference to IMD 10 and the components of IMD 10 described in FIG. 3. However, a person skilled in the art will understand that external device 12 and the components of external device 12 may determine the impedance score in some examples with input from IMD 10. In some examples, server 94 (e.g., a cloud server) may receive data from external device 12 or directly from IMD 10 and perform certain techniques of this disclosure.

With reference to FIG. 7, processing circuitry 50 may determine an adaptive threshold (120). The adaptive threshold includes a threshold that changes over time based on various attributes of patient 4 and the time at which the adaptive threshold is determined. As stated above, in some examples, one device, such as external device 12, may determine the adaptive threshold and transmit the adaptive threshold to another device, such as IMD 10. In such examples, processing circuitry 50 may determine the adaptive threshold as received from external device 12 in order to determine the impedance score.

In some examples, processing circuitry, e.g., processing circuitry 50 of IMD 10, processing circuitry 80 of external device 12, or processing circuitry 98 of server 94, may determine the adaptive threshold using a formula that takes into account statistical values of detected impedance signals over time. In some examples, the formula selected for calculating the adaptive threshold yields a threshold that is proportional to the absolute impedance value and the intraday variation of the impedance. For example, the formula may take into account the median and/or the average (e.g., a statistical representation) of the impedance signals received from electrodes 16. In a non-limiting example, processing circuitry 50 may determine the adaptive threshold on any given day as a sum of (a) an average of the impedance values in the last X number of days and {(b1) the average difference between the maximum and minimum impedances values tracked over the last X number of days or (b2) the average or median day-to-day impedance difference}. In some examples, processing circuitry 50 may select between (b1/2) component, such that the selection between the (b1/2) component is based on achieving a higher variability in data and meanwhile, reducing the recovery time for a patient. In the above example, X may be 7 days, 10 days, 30 days, 40 days, etc. In some examples, processing circuitry 50 may receive user input specifying the adaptive threshold value. In other words, the adaptive threshold may be programmable by a user.

In some examples, processing circuitry 50 may determine the statistical representation with reference to the time since implantation or the time since the fluid index values have been greater than zero (e.g., a first fluid index event). In some examples, processing circuitry 50 may determine an average of impedance values for each day based on all or a subset of all impedance values received over the course of a single day. Processing circuitry 50 may then calculate a median of the daily averages over a predetermined period of time, such as within X days of the first fluid index event, within X days of implantation, or within the last X number of days, where X may be a predetermined number of days. In a non-limiting example, X may be selected to be 30 days or 31 days. For example, processing circuitry 50 may determine the median of 30 daily averages determined within the last 30 days from the present day or from another day of interest.

In one example, the adaptive threshold formula may also take into account a median of the difference between a maximum impedance value and a minimum impedance value measured within X days of implantation, within X days of the first fluid index event, or within the last X number of days from the present day or from another day of interest. In a non-limiting example, X may be selected to be 30 days or 31 days. For example, the formula may calculate the range between the maximum impedance value and the minimum impedance value each day and determine a median value of the range over the predetermined period of time. In some examples, the range of the maximum and minimum impedance values may include the difference between the maximum impedance value measured within a predetermined period of time (e.g., last 30 days) and the minimum impedance value measured within the same period of time (e.g., last 30 days). In other examples, the range may include a difference between the daily maximum impedance value and the daily minimum impedance value. In such examples, the adaptive threshold formula may take into account the median of the range of impedance values measured over a predetermined period of time. For example, the adaptive threshold formula may use the median of the daily maximum and the daily minimum impedance values measured within the last 30 or 31 days. As such, processing circuitry, e.g., processing circuitry 50 of IMD 10, processing circuitry 80 of external device 12, or processing circuitry 98 of server 94, may determine the adaptive threshold based at least in part on the median of differences between one or more maximum tissue impedance values and one or more minimum tissue impedance values.

In one example, the adaptive threshold may include a combination of the considerations discussed above. For example, the adaptive threshold may be satisfied based on a summation of a calculated median of the average impedance values in the last 30 or 31 days and the median of the difference between (or range of) daily maximum impedance values and daily minimum impedance values measured in the last 30 or 31 days. In other words, the two median values for each part of the equation may be added together to determine the adaptive threshold.

With reference still to FIG. 7, processing circuitry, e.g., processing circuitry 50 of IMD 10, processing circuitry 80 of external device 12, or processing circuitry 98 of server 94, may determine fluid index values and average impedance values over a first time period (122). The first time period may be measured from a present day (e.g., within 10 days of today) or measured from another time of interest (e.g., from 5 pm the previous day, etc.). For example, processing circuitry 50 may determine a number of fluid index values in the last X number of days from the present day or from another time of interest. In such examples, processing circuitry 50 may determine at least one of an average impedance value of the one or more subcutaneous tissue impedance signals measured over a period of time, and one or more fluid index values based at least in part on the one or more reference impedance values and the at least one second tissue impedance value.

In some examples, processing circuitry 50 may also determine a number of average impedance values for the last X number of days. In some examples, the first time period may be set to include the last 30 days. In some examples, processing circuitry 50 may determine the average impedance value based on a subset of the at least one first tissue impedance value. For example, processing circuitry 50 may determine the impedance values for day 1, day 2, and through day 30 to determine an average of the impedance values for days 1-30.

Similarly, processing circuitry 50 may determine fluid index values and average impedance values over a second time period (124). The second time period may include less time than the first time period. For example, the first time period may include the last 30 days, whereas the second time period may include the last 7 days. Although described as being performed by processing circuitry 50, the fluid index value may in accordance with the techniques of FIG. 7, may be determined by any one or more of IMD 10, external device 12, or server 94, e.g., by the processing circuitry of any one or more of these devices.

With reference still to FIG. 7, processing circuitry 50 may determine weighting factors for the adaptive threshold (126). In some examples, the weighting factors may range from values of 0.1 and 4.5. In other examples, the weighting factors may be more or less than this general range, for example, depending on the particular formula used to calculate the adaptive threshold. IMD 10 may scale the adaptive threshold using the weighting factors based on the type of comparison being performed to determine one or more scoring thresholds. As such, the scoring thresholds include the adaptive threshold scaled by the one or more weighting factors. For example, IMD 10 may multiply the adaptive threshold by different weighting factors prior to comparing the fluid index values to the adaptive threshold. In some examples, the weighting factors and adaptive threshold may only be used with respect to fluid index values, whereas the average impedance values may be compared against a different threshold value that does not rely on weighting factors.

On a given day, processing circuitry 50 may determine anew or modify an impedance score when the fluid index values during the first time period satisfy the adaptive threshold multiplied by the corresponding weighting factors (128). In addition, processing circuitry 50 may determine anew or modify an impedance score when the average impedance satisfies an impedance threshold during the first time period.

In some examples, processing circuitry 50 may modify the impedance score by incrementing the impedance score by a set value. For example, processing circuitry 50 may modify the impedance score by adding a positive integer value to the impedance score. In a non-limiting example, processing circuitry 50 may modify the impedance score by adding a value of one to the impedance score in response to certain triggering events. Processing circuitry 50 may determine the impedance score anew where processing circuitry 50 has reset the impedance score to zero or where processing circuitry 50 has not already incremented the impedance score by any amount.

In some examples, processing circuitry, e.g., processing circuitry 50 of IMD 10, processing circuitry 80 of external device 12, or processing circuitry 98 of server 94, may determine satisfaction of at least one of: a scoring threshold and an impedance threshold, with respect to one or more time windows. For example, processing circuitry 50 modify the impedance score in response to the one or more fluid index values satisfying one or more scoring thresholds for at least one of: a predetermined amount of time and a predetermined number of times (e.g., number of days, etc.). In an illustrative example, processing circuitry 50 may increment the impedance score by a point value (e.g., a 1 point value) in response to the following example conditions (e.g., scoring thresholds) being satisfied with respect to the first time period: (1) the fluid index values in the last 30 days have been greater than or equal to the adaptive threshold (multiplied by 0.6) for one or more days; (2) the fluid index values in the last 30 days have been greater than or equal to the adaptive threshold (multiplied by 1.7) for one or more days; or (3) the fluid index values in the last 30 days have been greater than or equal to the adaptive threshold (multiplied by 3.2) for one or more days. In this example, processing circuitry 50 determined the weighting factors as 0.6, 1.7, and 3.2. In this example, the first time period is the last 30 days.

However, as discussed above, the time periods and the weighting factors may vary depending on specifics related to patient 4, for example.

In another example, processing circuitry 50 may also increment the impedance score by a point value of greater than one (e.g., two points) in response to the average impedance satisfying an impedance value threshold and the fluid index satisfying various scoring thresholds. In some examples, processing circuitry 50 may modify the impedance score in response to the average impedance value satisfying an impedance value threshold. The impedance value threshold may, in some examples, be less than or equal to approximately 600 ohms or another comparable ohm value. In any case, the impedance value threshold may be a user-defined variable.

For example, processing circuitry 50 may increment the impedance score by two points in response to the following example conditions (e.g., scoring thresholds and impedance value thresholds) being met with respect to the first time period: (1) the fluid index values in the last 30 days have been greater than or equal to the adaptive threshold (multiplied by 1.5) for 24 or more days; or (2) the average impedance in the last 30 days has been less than or equal to approximately 600 ohms. For the first condition, the 24 or more days may be consecutive days or instead may be a cumulative 24 days. For the average impedance, the average impedance in the last 30 days may refer to a set of daily average impedances in the last 30 days. In other examples, the average impedance in the last 30 days may refer to a single average of the impedance values measured over time. In other examples, the average impedance may refer to a single average of the daily average impedance values determined over time. In any event, the average impedance value may be an average of some of the impedance values IMD 10 has measured over time. For example, the average may be based on at least two impedance values measured by IMD 10. In some examples, the at least two impedance values may include one or more current impedance values and/or one or more historic impedance values.

In some examples, processing circuitry 50 may determine anew or modify an impedance score when the fluid index values during the second time period satisfy the adaptive threshold multiplied by the corresponding weighting factors (130). In addition, processing circuitry 50 may determine anew or modify an impedance score when the average impedance satisfies an impedance threshold during the second time period.

In an illustrative example, processing circuitry 50 may increment the impedance score by a point value equal to one in response to the following example conditions being satisfied with respect to the second time period: (1) the fluid index values in the last seven days have been greater than or equal to the adaptive threshold (multiplied by 0.6) for one or more days; (2) the fluid index values in the last seven days have been greater than or equal to the adaptive threshold (multiplied by 1.7) for one or more days; or (3) the fluid index values in the last seven days have been greater than or equal to the adaptive threshold (multiplied by 1.5) for seven or more days. In this example, processing circuitry 50 determined the weighting factors as 0.6, 1.7, and 1.5. In this example, the second time period is the last seven days. However, as discussed above, the time periods and the weighting factors may vary depending on specifics related to patient 4, for example. In addition, for the last condition, the 7 or more days may be consecutive days or instead may be a cumulative 7 days.

In another example, processing circuitry 50 may also increment the impedance score by a point value of greater than one (e.g., two points) in response to other example conditions being met with respect to the second time period: (1) the fluid index values in the last seven days have been greater than or equal to the adaptive threshold (multiplied by 3.2) for one or more days; or (2) the average impedance in the last seven days has been less than or equal to approximately 600 ohms. For the average impedance, the average impedance in the last 7 days may refer to a set of daily average impedances in the last 7 days. In other examples, the average impedance in the last 7 days may refer to a single average of the impedance values measured over time. In other examples, the average impedance may refer to a single average of the daily average impedance values determined over time.

In some examples, where overlaps exist between conditions, only the higher point value would be added to the impedance score so as to avoid any compounding affects to the modification of the impedance score. In keeping with the example described above, where two conditions are met (e.g., average impedance in last 7 days and in the last 30 days has been greater than or equal to approximately 600 ohms), the impedance score may only increment by two and not by four. In other examples, where two conditions are met (e.g., average impedance in last 7 days and in the last 30 days has been greater than or equal to approximately 600 ohms), processing circuitry 50 may increment the impedance score based on both conditions being satisfied.

Once the impedance score has been calculated for a given day, processing circuitry, e.g., processing circuitry 50 of IMD 10, processing circuitry 80 of external device 12, or processing circuitry 98 of server 94, may output the impedance score for further analysis (132). In one example, processing circuitry 50 of IMD 10 may output the impedance score to storage device 56. In other examples, processing circuitry 50 may output the impedance score to external device 12 via communication circuitry 54. In examples where external device 12 calculates the impedance score, external device 12 may output the impedance score from processing circuitry 80 to storage device 84. In some examples, external device 12 may output the impedance score to another device, such as to IMD 10, one of computing device 100 or server 94, for further analysis. In examples where server 94 calculates the impedance score, processing circuitry 98 may output the impedance score from processing circuitry 98 to storage device 96. In some examples, server 94 may output the impedance score to another device, such as to IMD 10 one of computing devices 100, or external device 12, for further analysis. For example, the impedance score may be used to determine the heart or health condition status of patient 4 as described in FIG. 6.

As noted before with respect to FIG. 6, the above techniques of FIG. 7 may also be performed on a periodic basis. For example, the impedance scores may be determined according to a resolution parameter setting of IMD 10 (e.g., the resolution parameter used to signal a frequency at which electrodes 16 should probe for impedance measurements). In other examples, the impedance score may be calculated irrespective of the resolution parameter, which, for example, may apply to the fluid index determination and/or the reference impedance value determination, but not the impedance score determination. For instance, IMD 10 may calculate the impedance scores at several time intervals each day (e.g., once in the morning, once in the afternoon, once in the evening, once after meals, etc.). IMD 10 may calculate the impedance score once a day, each week, every two weeks, each month, etc. In some examples, IMD 10 may also calculate the impedance score in response to a user command (e.g., from a physician, from a user interface) or in response to a satisfaction of another condition (e.g., based on activity level or other physiological parameters). For example, IMD 10 may determine impedance score on a per measurement basis, such as on a per fluid index determination basis or on a per impedance measurement basis. A person of skill in the art should appreciate that various periods may exist for when IMD 10 or external device 12 may transmit impedance scores, receive impedance scores, receive fluid index values, and/or otherwise, calculate impedance scores for subsequent analysis.

Turning now to FIG. 8, FIG. 8 is a flow diagram illustrating an example method for determining fluid index values. IMD 10 may determine fluid index values using impedance signals received from electrodes 16. In some examples, IMD 10 may determine fluid index values in accordance with U.S. application Ser. Nos. 12/184,149 and 12/184,003 by Sarkar et al., entitled "USING MULTIPLE DIAGNOSTIC PARAMETERS FOR PREDICTING HEART FAILURE EVENTS," and "DETECTING WORSENING HEART FAILURE BASED ON IMPEDANCE MEASUREMENTS," both filed on Jul. 31, 2008, both of which are incorporated herein by reference in their entirety. Although described as being performed by IMD 10, the example method of FIG. 8 may be performed by any one or more of IMD 10, external device 12, or server 94, e.g., by the processing circuitry of any one or more of these devices.

In some examples, processing circuitry, e.g., processing circuitry 50 of IMD 10, processing circuitry 80 of external device 12, or processing circuitry 98 of server 94, may maintain a buffer of impedance values and impedance statistics (140). For example, processing circuitry 50 may compute the fluid index over a finite time period that functions as a sliding window over which processing circuitry 50 computes the fluid index. Processing circuitry 50 may compute the fluid index daily over a period of several days, a week, or more. In such examples, processing circuitry 50 may store a buffer of daily fluid index values as fluid index values in storage device 56. In some examples, the buffer stores the previous daily fluid index values. In some examples, processing circuitry 50 may maintain a buffer, such as a FIFO buffer, for the last predetermined number of days. As such, processing circuitry 50 may maintain a buffer of the relative changes in the one or more subcutaneous tissue impedance signals over time.

In some examples, processing circuitry 50 may perform a comparison of the at least one second tissue impedance value to the one or more reference impedance values. In some examples, processing circuitry 50 may store the difference values between the reference and the daily impedance value in a buffer. That is, processing circuitry 50 may modify the buffer based at least in part on the comparison. In some examples, the buffer may include the last twelve to fifteen days of difference values. For example, the FIFO buffer may include the last 12 days of day-to-day impedance differences. In yet another example, the FIFO buffer may include the last 15 days of day-to-day impedance differences. The impedance differences refer to differences from a corresponding reference impedance value.

In some examples, processing circuitry, e.g., processing circuitry 50 of IMD 10, processing circuitry 80 of external device 12, or processing circuitry 98 of server 94, may begin calculating the fluid index after a predetermined number of days has passed from when IMD 10 was implanted in patient 4. As such, processing circuitry 50 may determine whether the predetermined amount of time has passed before calculating the fluid index (142). Until then, processing circuitry 50 may continue adding to the buffer and even after the predetermined number of days, processing circuitry 50 may continue adding to the buffer. In some instances, the predetermined number of days is 16 days, meaning processing circuitry 50 may not determine a first reference impedance value until day 16 after implant. As such, processing circuitry 50 may determine a first fluid index value based on a comparison of the reference impedance value and the daily impedance values. While specific numbers of days, such as 16 days in this example, are used or ranges of days are used in certain examples of this disclosure, the techniques of this disclosure are not so limited, and other examples may include other suitable ranges or threshold numbers. For example, processing circuitry 50 may estimate the first reference impedance value at day 6 after implant or in another example, may wait longer than 16 days, such as 20 days before estimating the first reference point. In some examples, processing circuitry 50 may estimate the first reference impedance value 13 days after implant. Example reference impedance values are shown with reference to FIG. 9.

Before the predetermined amount of time has passed, processing circuitry 50 may analyze impedance changes over time before determining a first fluid index value (144). For example, processing circuitry 50 may determine statistical representations of the impedance values over time. In one example, processing circuitry 50 may compute the difference between the current measured impedance value and each of the values in the buffer of previous daily measured impedance values. As such, processing circuitry 50 may determine the median of these difference values. This value is referred to as "MED_VAR" and may be stored in storage device 56 as a variability value.

In some examples, processing circuitry, e.g., processing circuitry 50 of IMD 10, processing circuitry 80 of external device 12, or processing circuitry 98 of server 94, may determine a scaling factor for impedance changes over time and a duration counter (146). For example, processing circuitry 50 may determine a variability value, VAR_VAL, based on the final averaged value and past daily measured impedance values. Processing circuitry 50 may compute the difference between the current measured impedance value and each of the values in the buffer of previous daily measured impedance values. In some examples, the variability value is not time dependent and, thus, MED_VAR=VAR_VAL.

In some examples, the variability value may be time dependent. In such examples, the time dependent value, VAR_FRAC, may be determined using a piecewise linear function, or any other mathematical function, e.g., an exponential decay. The variability value may be the product of median of the differences in daily impedance values stored in the buffer (e.g., MED_VAR) and the time dependent value (VAR_FRAC), i.e., VAR_VAL=MED_VAR*VAR_FRAC.

An example piecewise linear function is:

$$VAR\_FRAC = \begin{cases} 0, & \text{if } x < 5 \text{ or } x > 90 \\ 1.25, & \text{if } 5 \leq x \leq 30 \\ 1.0, & \text{if } 30 < x \leq 60 \\ 0.5, & \text{if } 60 < x \leq 90 \end{cases}$$

where 'x' represents time measured in days from the start of the present fluid index event (e.g., the number of days that the fluid index has been greater than 0 or the number of days since the daily mean value has been less than the daily reference value).

In some examples, processing circuitry 50 may utilize a duration counter to keep track of the number of days passed since the fluid index has been greater than zero and store the value in storage device 56. Thus, processing circuitry 50 may access the time value from storage device 56 when calculating the variability value.

In an example, processing circuitry 50 may implement a duration counter that counts the number of days since the fluid index began computing. For example, the count reading for the duration counter may represent the number of days that the fluid index has been above a fluid index threshold. In some examples, the fluid index threshold is zero. In such examples, the count reading for the duration counter may represent the number of days that the fluid index has maintained a positive value without resetting. Processing circuitry 50 may use a running tally to calculate the duration count. In such examples, processing circuitry 50 counts the number of days since the measured impedance (or a mean or other value determined based thereon) was less than the reference impedance. Processing circuitry 50 may reset the duration counter (e.g., to 0) at any time when the fluid index equals zero. In other examples, the duration counter may increment using a hysteresis function for the fluid index threshold, such that the duration counter will reset if the fluid index falls below a predetermined value, such as 1 or 2. Additionally, duration counter may not begin incrementing until the fluid index has been above a predetermined value for a specified amount of time.

In some examples, processing circuitry 50 may determine impedance difference values and modify the buffer (148). For example, processing circuitry 50 determines reference impedance values that are associated with measured impedance values (e.g., historical impedance values). In particular, the reference impedance values generally track the trend of measured impedance values. As an example, processing circuitry 50 may calculate a reference impedance value by first retrieving the current impedance value and reference impedance value from storage device 56 (stored as measured impedance values and reference impedance values) and comparing the values to each other. Because the reference impedance value tracks the measured impedance value, the comparison may be used to determine whether to calculate the new or current reference value by either increasing or decreasing the old or previous reference impedance value. Processing circuitry 50 may store current and previous reference values in storage device 56 as reference impedance values.

In general, processing circuitry 50 may adapt the rate of change of the reference impedance over time. In particular, this method allows for the reference impedance to increase and decrease at different rates over the same period of time and to increase and decrease at different rates over time. As previously described, this is achieved by storing groups of preselected or predetermined increment and decrement values. Each group of values corresponds to a specific period time. The increment value of each group is used as a positive slope value, i.e., used to increase the value of the reference impedance. The decrement value of each group is used as a negative slope value, i.e., used to decrease the value of the reference impedance.

Processing circuitry 50 may also store a plurality of increment and decrement values, referred to as slope values, in storage device 56. Example slope values are discussed above with reference to drift up and drift down parameters.

The slope values are used to calculate a current reference impedance value from a previous reference impedance value. In some examples, the plurality of slope values includes a plurality of groups of slope values. Each group of slope values corresponds to a period of time and includes a predetermined increment value and a predetermined decrement value.

In some examples, processing circuitry 50 may adjust the increment parameter and the decrement parameter in a piece-wise linear fashion to accommodate for the rapid rise of impedance in the months following implantation.

Processing circuitry 50 selects a particular group based on the time and selects either the first or second slope value from the selected group based on the comparison of the current measured impedance value to the corresponding reference impedance value. Processing circuitry 50 selects the increment value from the selected group when the current measured impedance value is greater than the reference impedance value. Similarly, when the current measured impedance value is less than the reference impedance value, processing circuitry 50 selects the decrement value from the selected group.

Processing circuitry 50 may, for example, store two groups of slope values. A first group may be utilized during the first 34-60 days following implantation of IMD 10 in patient 4. The second group may be utilized during the next 61-120 days. These periods are merely examples, and other periods and numbers of slope value groups are contemplated.

Selecting slope values in this way may allow for more accurate tracking of subcutaneous tissue impedance values as the device pocket dries out following implantation of IMD 10. This is because the fluid build-up in the device pocket immediately following the implant procedure results in a lower impedance than normal. As the fluid dissipates the impedance increases. The rate at which the fluid dissipates decreases as time elapses so it may be desirable for the reference impedance to be able to change at a different rate immediately following implantation compared to after 60, 100, or 120 days have passed. Similarly, it may be desirable to change the rate at which the reference impedance changes over time.

When processing circuitry 50 determines that the predetermined amount of time has passed since implantation, processing circuitry 50 may calculate the fluid index (142). Processing circuitry 50 computes the fluid index using measured and reference impedance values stored in storage device 56, i.e., first impedance values and second impedance values. Processing circuitry 50 may store the computed value as one or more fluid index values in storage device 56. As stated before, the fluid index calculation techniques may be performed by any one or more of IMD 10, external device 12, or server 94, e.g., by the processing circuitry of any one or more of these devices.

For example, processing circuitry 50 may compute the fluid index as a function of the difference between the measured impedance value and the reference impedance value when the measured impedance value is less than the reference impedance value. As an example, processing circuitry 50 may compute the fluid index simply as the difference between the measured impedance value and the reference impedance value when the measured impedance value is less than the reference impedance value.

In some examples, processing circuitry 50 may determine fluid index values by summing buffer values. For example, the total fluid index value is the sum of the all the daily fluid index values in the FIFO buffer. Because the size of the buffer is constant, the buffer operates as a sliding window in time over which the fluid index is determined, e.g., as the current daily fluid index is added, the least recent value in the buffer is removed.

In some examples, processing circuitry 50 may determine that a buffer reset condition has been satisfied. For example, when the current impedance is greater than the reference impedance, processing circuitry 50 resets the fluid index buffer. For example, processing circuitry 50 may reset the fluid index, i.e., reset the buffer, when the daily measured impedance value is greater than or equal to the reference impedance value. In some examples, processing circuitry 50 may reset the fluid index, i.e., reset the buffer, when the daily mean impedance value (e.g., the average of impedance values measured in a 24-hour period) is greater than or equal to the daily reference impedance value. In any case, processing circuitry 50 may reset the buffer in response to the buffer reset condition being satisfied.

Processing circuitry 50 may determine one or more fluid index values based at least in part on the buffer. For example, processing circuitry 50 determines the fluid index on any day as the sum of the FIFO buffer values. In some examples, processing circuitry 50 may determine a time-dependent value and adjust the fluid index values (152). For example, the time-dependent value may be added to the fluid index depending on the time that the fluid index has maintained a positive value without resetting. The time-dependent value may increase as a linear, piecewise linear, exponential, or other function of the duration counter.

In some examples, the time-dependent value added on any day is equal to a constant duration parameter multiplied by the duration counter minus 30, where that product may then be multiplied by a drift-down nominal value or another drift down value. In keeping with the example above, where the drift-down nominal value is equal to 0.05 and where the constant duration parameter is equal to 1.0, the time-dependent value would be equal to 1.0 times 0.05 times (the duration counter minus 30). Processing circuitry 50 may then add the time-dependent value to the fluid index value.

In some examples, processing circuitry 50 may then store the fluid index values to storage device 56 (154). In other examples, processing circuitry 50 may output the fluid index to external device 12 via communication circuitry 54. In examples where external device 12 calculates the fluid index based on data received from IMD 10, external device 12 may output the fluid index from processing circuitry 80 to storage device 84. In other examples, external device 12 may output the fluid index to another device, such as to IMD 10, for further analysis. For example, either IMD 10 or external device 12 may use the fluid index values to determine the impedance score and/or heart condition status of patient 4, as described in FIGS. 6 and 7.

In some examples, processing circuitry 50 may reset the reference impedance in response to identifying a fluid index reset condition (156). Processing circuitry 50 may reset the reference impedance values at any given time as part of a reference reset protocol. For example, processing circuitry 50 may identify a fluid index reset condition that causes at least one reference impedance value to reset to a baseline value. In some examples, the at least one reference impedance value includes a current reference impedance value that processing circuitry 50 has most recently determined. In another example, the at least one reference impedance value includes a fluid index value that processing circuitry 50 is in the process of determining, and as such, processing circuitry 50 may cause the one or more reference impedance values to be set to the baseline value while processing circuitry 50 is performing the determination.

In some instances, the baseline value may be a value of zero, such that the fluid index value resets to zero. In some examples, the baseline value may be a non-zero value, such as a positive or negative value. In some examples, processing circuitry 50 may cause the fluid index value to reset to the baseline value by adjusting the reference impedance value to a reference impedance baseline value. That is, when processing circuitry 50 performs the comparison of the reference impedance values to the fluid index, processing circuitry 50 may cause one or more of the reference impedance values to be less than or equal to the daily average impedance value, such that all or part of the FIFO buffer is cleared. In one example, processing circuitry 50 may adjust the drift-up or drift down parameters used to calculate reference slopes in order to cause a daily reference impedance value to be less than or equal to a daily average impedance value, thereby resetting the fluid index value to a baseline fluid index value.

In some examples, processing circuitry 50 may receive, via communication circuitry 54, a reset signal indicating that the reference impedance value is to reset to the baseline value. In response to receiving the reset signal, processing circuitry 50 may reset the reference impedance value. In some examples, processing circuitry 50 may receive a manual reset request from a physician or patient via a user interface (e.g., of external device 12 or of one of computing devices 100). For example, a physician may determine that the patient has reached a new equilibrium (or normal state) for impedance (e.g., after a new medication change). As such, the physician may elect to cause transmission of the manual reset request to processing circuitry, e.g., processing circuitry 50 of IMD 10, processing circuitry 80 of external device 12, or processing circuitry 98 of server 94, thereby causing a fluid index reset condition. In such examples, processing circuitry 50 may receive the manual reset request and identify the fluid index reset condition. In response to receiving the manual reset request, processing circuitry 50 may identify a fluid index reset condition and cause the reference impedance value to reset to a baseline value. For example, processing circuitry 50 may cause the reference impedance value to reset to zero by clearing a FIFO buffer, such that the accumulation of values in the FIFO buffer equals zero.

In some examples, processing circuitry 50 may identify a fluid index reset condition based on data received from processing circuitry 50. For example, processing circuitry 50 may automatically detect physiologic or in some cases non-physiologic, changes in impedance. In one example non-physiologic change, processing circuitry 50 may determine that a change in position or orientation of IMD 10 has occurred. In some examples, IMD 10 may determine whether the orientation of IMD 10 has changed more than a predefined amount. For example, processing circuitry 50 may use changes in measured impedance values to determine whether the IMD 10 has flipped or otherwise changed orientation.

In some examples, processing circuitry 50 may use accelerometer data to determine the IMD orientation. For example, processing circuitry 50 may identify relative changes between various accelerometer values to determine whether the IMD orientation satisfies a predefined IMD orientation threshold. The IMD orientation threshold may be set such that the threshold is satisfied when IMD 10 is orientated perpendicularly facing toward skin or perpendicularly facing toward muscle layer, etc. In another example, IMD orientation threshold may be set such that the threshold is satisfied when the orientation of IMD 10 indicates that patient 4 is oriented upright, laying down, at an incline, face downward while laying, etc.

In some examples, processing circuitry 50 may cause a fluid index reset based on such changes in position or orientation, depending on the nature of the change. For example, if IMD 10 changes position such that electrodes 16 now face a different direction, such as toward muscle layer 20 rather than outward toward skin layer 18, then processing circuitry 50 may reset the fluid index calculations by causing a fluid index reset condition. As such, processing circuitry 50 may identify the fluid index reset condition upon processing circuitry 50 determining that the orientation of IMD 10 has changed more than the predefined amount, such as to indicate, for example, that the orientation of IMD 10 is different than previously recorded. In such examples, processing circuitry 50 may reset the fluid index to a baseline value upon identifying a change in orientation of IMD 10, where the change is satisfies a threshold, such as by changing more than 45 degrees or 90 degrees clockwise or counterclockwise, changing 108 degrees, etc.

In one example, processing circuitry 50 may determine such changes in position based on particular impedance changes or changes in average impedance values. For example, processing circuitry 50 may automatically detect a change in position of IMD 10 based on single-day changes in impedance that exceed a particular amount. In some examples, processing circuitry 50 may determine such impedance value changes based on a step function in a X day before and after a moving impedance value average. In another example, processing circuitry 50 may detect that a position of IMD 10 has changed based on signals received from a 3-axis accelerometer integrated as part of IMD 10. For example, processing circuitry 50 may detect changes in signals received from the accelerometer and determine that IMD 10 has flipped, such that electrodes 16 are now facing a different direction than previously. Processing circuitry 50, upon detecting such activity of IMD 10, may reset the fluid index values to the baseline value.

As noted before with respect to FIGS. 6 and 7, the above techniques of FIG. 8 may be performed on a periodic basis. For example, the fluid index values may be determined according to a resolution parameter setting of processing circuitry 50 (e.g., the resolution parameter used to signal a frequency at which electrodes 16 should probe for impedance measurements). In other examples, the fluid index value may be calculated irrespective of the resolution parameter, which, for example, may apply to the impedance score determination and/or the reference impedance value determination, but not the fluid index determination. For instance, processing circuitry 50 may calculate the fluid index values at several time intervals each day (e.g., once in the morning, once in the afternoon, once in the evening, once after meals, etc.). Processing circuitry 50 may calculate the fluid index values once a day, each week, every two weeks, each month, etc. In some examples, processing circuitry 50 may also calculate the fluid index values in response to a user command (e.g., from a physician, from a user interface) or in response to a satisfaction of another condition (e.g., based on activity level or other physiological parameters). For example, processing circuitry 50 may determine fluid index values on a per measurement basis, such as on a per impedance score determination basis or on a per impedance measurement basis. A person of skill in the art will appreciate that various periods may exist for when processing circuitry 50 or external device 12 may transmit fluid index values, receive fluid index values and/or otherwise, calculate fluid index values for subsequent analysis.

FIG. 9 is a timing diagram illustrating use of a finite buffer to limit accumulation of a fluid index over time. FIG. 9 illustrates a sudden drop in measured impedance values 920 followed by a trend of increasing impedance back towards a baseline or reference impedance 922. Although described in terms of processing circuitry 50 comparing measured impedance measurements to reference impedance measurements to determine difference values, the example of FIG. 9 may involve any one or more of IMD 10, external device 12, or server 94, e.g., by the processing circuitry of any one or more of these devices.

In an example in which a finite buffer would not be used, all differences between the measured impedances and reference impedances while the measured impedances are less than the reference impedances, as indicated by the lighter shaded area 950 between the measured and reference impedances, are summed. For instance, the non-finite buffer in the example of FIG. 9 corresponds to start of the fluid index event from time period 948 onward. As a result, the corresponding fluid index 952 continues to increase, despite increasing impedance, which may indicate an improvement in patient condition due to, for example, improved compliance with medication or diet. Accordingly, processing circuitry 50 or another device may provide an alert, due to the fluid index 952 crossing a threshold, while the condition of patient 4 is actually improving, or may include the increasing fluid index 952 in determining the impedance score, rather than limiting the fluid index to a finite buffer.

In an example in which a finite buffer is used, a finite number, e.g., sliding window, of differences between the measured impedances and reference impedances while the measured impedances are less than the reference impedances, as indicated by the darker shaded area 954 between the measured and reference impedances, are summed. For instance, the finite buffer in the example of FIG. 9 corresponds to sliding time period 955, in which processing circuitry 50 has not encountered a buffer reset condition and so the time period 955 continues to slide from the left of the page to the right. As a result, the corresponding fluid index 956 begins to decrease while the measured impedances increase and the condition of the patient improves. Accordingly, processing circuitry 50 or another device may avoid providing an alert while the condition of patient 4 is actually improving.

Figure 10:
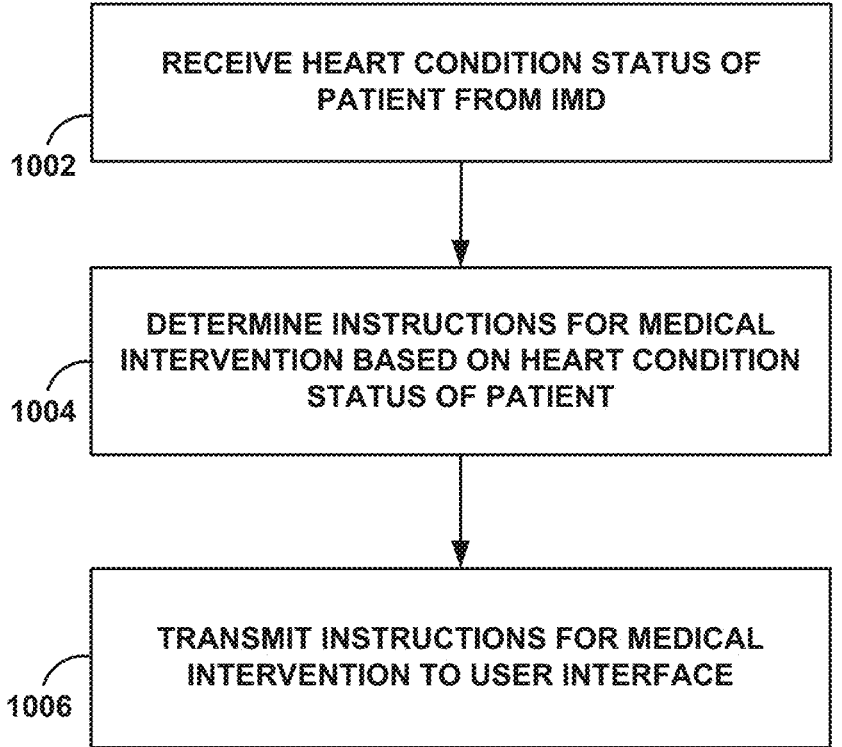
FIG. 10 is a flow diagram illustrating an example method that may be performed by one or both the IMD and external device shown in FIG. 1 to provide an alert to the patient with respect to a heart condition status of the patient, in accordance with one or more techniques disclosed herein.

Turning now to FIG. 10, external device 12 may receive the heart or health condition status of patient 4 from IMD 10 (1002). In some examples, external device 12 may determine the heart condition status and receive other data, such as raw impedance values, from processing circuitry 50. Although described as being generally performed by IMD 10, the example method of FIG. 10 may be performed by any one or more of IMD 10, external device 12, or server 94, e.g., by the processing circuitry of any one or more of these devices.

External device 12 may determine instructions for medical intervention based on the heart condition status of patient 4 (1004). For example, if the impedance score is greater than a high-risk threshold, external device 12 may determine instructions for medical intervention based on the high-risk determination. In other examples, external device 12 may determine different instructions for different risk levels or categories. For example, external device 12 may determine a first set of instructions for a high-risk patient and a second set of instructions for a medium risk patient. In some examples, external device 12 may not determine any instructions for a low risk patient (e.g., impedance score=0). In some examples, external device 12 may provide an alert, such as a text- or graphics-based notification, a visual notification, etc. In some examples, external device 12 may sound an audible or tactile alarm for patient 4, alerting them of the determined level of risk. In other examples, external device 12 may provide a visual light indication, such as emitting a red light for high risk or a yellow light for medium risk. The alert may indicate a possible or predicted heart failure decompensation event.

In some examples, external device 12 may transmit the instructions for medical intervention to a user interface (1006). In other examples, external device 12 may transmit the instructions to a device of a caretaker, such as a pager. In examples where processing circuitry 50 generates the instructions based on the heart condition status, IMD 10 may transmit the instructions for medical intervention to a user interface. The instructions may include the impedance score or may include the heart condition status determined from the impedance score. In some instances, a physician or caretaker may not need to know the actual impedance score value and may only want to receive the heart condition status determined from the impedance score. In some examples, external device 12, IMD 10, server 94, or computing devices 100 may use the impedance score to predict adverse health events using integrated diagnostic methods as described in commonly-assigned and co-pending application by Sarkar et al., entitled "DETERMINING LIKELIHOOD OF AN ADVERSE HEALTH EVENT BASED ON VARIOUS PHYSIOLOGICAL DIAGNOSTIC STATES," filed on even date herewith, and incorporated herein by reference in its entirety.

Various examples have been described. However, one skilled in the art will appreciate that various modifications may be made to the described examples without departing from the scope of the claims. For example, although described primarily with reference to subcutaneous impedance, in some examples other physiological parameters may be considered with subcutaneous impedance to detect worsening heart failure. Examples of other physiological parameters and techniques for detecting worsening heart failure based on these parameters in combination with impedance are described in commonly-assigned U.S. application Ser. Nos. 12/184,149 and 12/184,003 by Sarkar et al., entitled "USING MULTIPLE DIAGNOSTIC PARAMETERS FOR PREDICTING HEART FAILURE EVENTS," and "DETECTING WORSENING HEART FAILURE BASED ON IMPEDANCE MEASUREMENTS," both filed on Jul. 31, 2008, both of which are incorporated herein by reference in their entirety.

Illustrative examples of the disclosure include:

Example 1: A system for detecting statuses of health conditions, the system including: an implantable medical device (IMD) including a plurality of electrodes and configured for subcutaneous implantation, wherein the IMD is configured to receive one or more subcutaneous tissue impedance signals from the electrodes; and processing circuitry configured to: determine, based at least in part on the one or more subcutaneous tissue impedance signals, a plurality of tissue impedance values; determine, based at least in part on the plurality of tissue impedance values, a fluid index value and an average impedance value; determine an impedance score based at least in part on the fluid index value and the average impedance value; and determine a health condition status of the patient based at least in part on the impedance score, wherein the processing circuitry is further configured to: identify a fluid index reset condition;

and reset the fluid index value to a baseline value in response to identifying the fluid index reset condition.

Example 2: A system according to Example 1, wherein the processing circuitry is configured to: receive a manual reset request; and identify the fluid index reset condition in response to receiving the manual reset request.

Example 3: The system according to any one of Examples 1 or 2, wherein the processing circuitry is configured to: identify an occurrence of one or more missing impedance values; and interpolate or extrapolate data from the plurality of tissue impedance values to include with the plurality of tissue impedance values as interpolated or extrapolated data.

Example 4: A system according to any one or more of Examples 1 through 3, wherein the processing circuitry is configured to: determine at least one additional impedance value in response to receiving a signal from a sensor device.

Example 5: A system according to any one or more of Examples 1 through 4, wherein the processing circuitry is configured to: identify an accelerometer value; determine that the accelerometer value satisfies an orientation threshold; and determine the plurality of tissue impedance values based at least in part on the determination that the accelerometer value satisfies the orientation threshold.

Example 6: A system according to any one or more of Examples 1 through 5, wherein the processing circuitry is configured to: identify a change in orientation of the IMD; determine that the change in orientation of the IMD satisfies a threshold; and identify the fluid index reset condition based at least in part on the determination that the change in orientation satisfies the threshold.

Example 7: A system according to any one of Examples 5 or 6, wherein the processing circuitry is configured to: determine the IMD orientation based on at least one of: a change in measured impedance values or accelerometer data.

Example 8: A system according to any one or more of Examples 1 through 7, wherein the processing circuitry is configured to: receive a plurality of signals using the electrodes, wherein the signals include the one or more subcutaneous tissue impedance signals and at least one ECG.

Example 9: A system according to any one or more of Examples 1 through 8, wherein the processing circuitry is configured to: receive intra-vascular impedance measurements; and determine the impedance score using one or more of the intra-vascular impedance measurements and the plurality of tissue impedance values.

Example 10: A system according to any one or more of Examples 1 through 9, wherein the processing circuitry is configured to: determine, based at least in part on the one or more subcutaneous tissue impedance signals, at least one first tissue impedance value that corresponds to a first time period; determine, based at least in part on the one or more subcutaneous tissue impedance signals, at least one second tissue impedance value that corresponds to a second time period different from the first time period; determine, based at least in part on the at least one first tissue impedance value, one or more reference impedance values; determine the fluid index value based at least in part on the one or more reference impedance values and the at least one second tissue impedance value; and determine the impedance score based on at least one of: the fluid index value or the average impedance value, wherein the IMD is configured for subcutaneous implantation outside of a thorax of the patient, and wherein the health condition status includes a heart condition status.

Example 11: A method of detecting statuses of health conditions, the method including: determining, based at least in part on one or more subcutaneous tissue impedance signals, a plurality of tissue impedance values, the one or more subcutaneous tissue impedance signals received from at least one electrode of an IMD disposed in a subcutaneous layer of a patient; determining, based at least in part on the plurality of tissue impedance values, a fluid index value and an average impedance value; determining an impedance score based at least in part on the fluid index value and average impedance value; and determining a health condition status of the patient based at least in part on the impedance score, wherein the method further includes: identifying a fluid index reset condition; and resetting the fluid index value to a baseline value in response to identifying the fluid index reset condition.

Example 12: A method according to Example 11, wherein the at least one electrode is implanted outside of a thorax of the patient.

Example 13: A method according to any one or more of Examples 11 or 12, wherein the at least one electrode contacts interstitial fluid in subcutaneous space.

Example 14: A method according to any one or more of Examples 11 through 13, further including: receiving a manual reset request; and identifying the fluid index reset condition in response to receiving the manual reset request.

Example 15: A method according to any one or more of Examples 11 through 14, further including: identifying an occurrence of one or more missing impedance values; and interpolating or extrapolating data from the plurality of tissue impedance values to include with the plurality of tissue impedance values as interpolated or extrapolated data.

Example 16: A method according to any one or more of Examples 11 through 15, further including: determining at least additional tissue impedance value in response to receiving a signal from a sensor device.

Example 17: A method according to any one or more of Examples 11 through 16, further including: identifying an accelerometer value; determining that the accelerometer value satisfies an orientation threshold; and determining the plurality of tissue impedance values based at least in part on the determination that the accelerometer value satisfies the orientation threshold.

Example 18: A method according to any one or more of Examples 11 through 17, further including: identifying a change in orientation of the IMD; determining that the change in orientation of the IMD satisfies a threshold; and identifying the fluid index reset condition based at least in part on the determination that the change in orientation satisfies the threshold.

Example 19: A method according to any one of Examples 17 or 18, further including: determining at least one of: the IMD orientation or the change in orientation of the IMD based on at least one of: a change in measured impedance values or accelerometer data.

Example 20: A method according to any one or more of Examples 11 through 19, further including: receiving a plurality of signals using the electrodes, wherein the signals include the one or more subcutaneous tissue impedance signals and at least one ECG.

Example 21: A non-transitory computer-readable storage medium having stored thereon instructions that, when executed, cause one or more processors to at least: determine, based at least in part on one or more subcutaneous tissue impedance signals, a plurality of tissue impedance values; determine, based at least in part on the plurality of tissue impedance values, a fluid index value and an average impedance value; determine an impedance score based at least in part on the fluid index value and average impedance value; determine a health condition status based at least in part on the impedance score; identify a fluid index reset condition; and reset the fluid index value to a baseline value.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry (as in QRS complex), as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, ROM, NVRAM, DRAM, SRAM, Flash memory, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Furthermore, although described primarily with reference to examples that provide an impedance score to indicate worsening heart failure in response to detecting impedance changes, other examples may additionally or alternatively automatically modify a therapy in response to detecting worsening heart failure in the patient. The therapy may be, as examples, a substance delivered by an implantable pump, cardiac resynchronization therapy, refractory period stimulation, or cardiac potentiation therapy. These and other examples are within the scope of the following claims.

The invention claimed is:

1. A system comprising:
an insertable cardiac monitor (ICM) comprising a housing and a plurality of electrodes on the housing, wherein the ICM, the housing, and the plurality of electrodes are configured for subcutaneous implantation in a patient, wherein at least two electrodes of the plurality of electrodes are positioned within 5 centimeters (cm) apart on the housing, wherein the ICM is configured to determine one or more subcutaneous tissue impedance signals of interstitial fluid measured using only the plurality of electrodes on the housing; and
processing circuitry configured to periodically:

determine, based at least in part on the one or more subcutaneous tissue impedance signals, a plurality of tissue impedance values;
determine, based at least in part on the plurality of tissue impedance values, one or more fluid index values;
determine an adaptive threshold based on an absolute impedance value of at least one of the one or more subcutaneous tissue impedance signals;
perform a comparison of the one or more fluid index values and the adaptive threshold; and
determine a health condition status of the patient based at least in part on the comparison.

2. The system of claim 1, wherein the processing circuitry is further configured to:
identify a fluid index reset condition; and
reset a fluid index value of the one or more fluid index values to a baseline value in response to identifying the fluid index reset condition.

3. The system of claim 2, wherein the processing circuitry is configured to:
receive a manual reset request; and
identify the fluid index reset condition in response to receiving the manual reset request.

4. The system of claim 2, wherein the processing circuitry is configured to:
identify a change in orientation of the ICM;
determine that the change in orientation of the ICM satisfies a threshold; and
identify the fluid index reset condition based at least in part on the determination that the change in orientation satisfies the threshold.

5. The system of claim 4, wherein the processing circuitry is configured to:
determine the ICM orientation based on at least one of: a change in measured impedance values or accelerometer data.

6. The system of claim 1, wherein the processing circuitry is configured to:
determine the health condition status satisfies a health condition worsening threshold; and
generate a remediation action in response to the determination that the health condition status satisfies the health condition worsening threshold.

7. The system of claim 6, wherein the remediation action includes modifying a therapy.

8. The system of claim 1, wherein the processing circuitry is configured to:
identify an occurrence of one or more missing impedance values; and
interpolate or extrapolate data from the plurality of tissue impedance values to include with the plurality of tissue impedance values as interpolated or extrapolated data.

9. The system of claim 1, wherein the processing circuitry is configured to:
determine at least one additional impedance value in response to receiving a signal from a sensor device.

10. The system of claim 1, wherein the processing circuitry is configured to:
identify an accelerometer value;
determine that the accelerometer value satisfies an orientation threshold; and
determine the plurality of tissue impedance values based at least in part on the determination that the accelerometer value satisfies the orientation threshold.

11. The system of claim 1, wherein the processing circuitry is configured to:

receive a plurality of signals using the electrodes, wherein the signals include the one or more subcutaneous tissue impedance signals and at least one electrocardiogram (ECG).

12. The system of claim 1, wherein the processing circuitry is configured to:

receive intra-vascular impedance measurements; and determine the one or more fluid index values using one or more of the intra-vascular impedance measurements and the plurality of tissue impedance values.

13. The system of claim 1, wherein the processing circuitry is configured to:

determine, based at least in part on the one or more subcutaneous tissue impedance signals, at least one first tissue impedance value that corresponds to a first time period;

determine, based at least in part on the one or more subcutaneous tissue impedance signals, at least one second tissue impedance value that corresponds to a second time period different from the first time period;

determine, based at least in part on the at least one first tissue impedance value, one or more reference impedance values; and determine the one or more fluid index values based at least in part on the one or more reference impedance values and the at least one second tissue impedance value.

14. The system of claim 1, wherein the at least two electrodes are positioned on the housing to face a skin layer of the patient when the ICM is subcutaneously implanted.

15. The system of claim 1, wherein at least two electrodes of the plurality of electrodes are separated by a fixed distance.

16. The system of claim 1, wherein the processing circuitry is further configured to:

determine an impedance score based at least in part on the comparison; and determine the health condition status of the patient based at least in part on the impedance score.

17. The system of claim 13, wherein the processing circuitry is further configured to:

determine the at least one second tissue impedance value is less than the one or more reference impedance values;

in response to the determination that the at least one second tissue impedance value is less than the one or more reference impedance values:

determine the adaptive threshold based on at least one of a mean or median of an absolute impedance value of the one or more impedance signals of subcutaneous interstitial fluid during a particular period of time, the particular period of time being within 30 days prior to the measurement of the one or more impedance signals of subcutaneous interstitial fluid;

compare the one or more fluid index values to the adaptive threshold; and modify the determination of the health condition status based on the comparison of the one or more fluid index values to the adaptive threshold.

18. A method for controlling operation of processing circuitry of a computing device comprising:

determining, by using the processing circuitry, based at least in part on one or more subcutaneous tissue impedance signals of interstitial fluid, a plurality of tissue impedance values, the one or more subcutaneous tissue impedance signals of interstitial fluid being measured using only a plurality of electrodes on a housing of an insertable cardiac monitor (ICM) disposed in a subcutaneous layer of a patient, wherein at least two electrodes of the plurality of electrodes are positioned within 5 centimeters (cm) apart on the housing;

determining, by using the processing circuitry, based at least in part on the plurality of tissue impedance values, one or more fluid index values determining, by using the processing circuitry, an adaptive threshold based on an absolute impedance value of at least one of the one or more subcutaneous tissue impedance signals;

performing, by using the processing circuitry, a comparison of the one or more fluid index values and the adaptive threshold; and determining, by using the processing circuitry, a health condition status of the patient based at least in part on the comparison.

19. The method of claim 18 for controlling operation of processing circuitry of a computing device, further comprising:

identifying, by using the processing circuitry, a change in orientation of the ICM;

determining, by using the processing circuitry, that the change in orientation of the ICM satisfies a threshold; and identifying, by using the processing circuitry, a fluid index reset condition based at least in part on the determination that the change in orientation satisfies the threshold; and resetting, by using the processing circuitry, a fluid index value of the one or more fluid index values to a baseline value in response to identifying the fluid index reset condition.

20. The method of claim 19 for controlling operation of processing circuitry of a computing device, further comprising:

determining, by using the processing circuitry, at least one of: the ICM orientation or the change in orientation of the ICM based on at least one of: a change in measured impedance values or accelerometer data.

21. The method of claim 18 for controlling operation of processing circuitry of a computing device, wherein the plurality of electrodes contact interstitial fluid in subcutaneous space.

22. The method of claim 18 for controlling operation of processing circuitry of a computing device, further comprising:

receiving, by using the processing circuitry, a manual reset request; and identifying, by using the processing circuitry, a fluid index reset condition in response to receiving the manual reset request; and resetting, by using the processing circuitry, a fluid index value of the one or more fluid index values to a baseline value in response to identifying the fluid index reset condition.

23. The method of claim 18 for controlling operation of processing circuitry of a computing device, further comprising:

identifying, by using the processing circuitry, an occurrence of one or more missing impedance values; and interpolating or extrapolating, by using the processing circuitry, data from the plurality of tissue impedance values to include with the plurality of tissue impedance values as interpolated or extrapolated data.

24. The method of claim 18 for controlling operation of processing circuitry of a computing device, further comprising:

determining, by using the processing circuitry, at least additional tissue impedance value in response to receiving a signal from a sensor device.

25. The method of claim 18 for controlling operation of processing circuitry of a computing device, further comprising:

identifying, by using the processing circuitry, an accelerometer value;

determining, by using the processing circuitry, that the accelerometer value satisfies an orientation threshold; and determining, by using the processing circuitry, the plurality of tissue impedance values based at least in part on the determination that the accelerometer value satisfies the orientation threshold.

26. The method of claim 18 for controlling operation of: processing circuitry of a computing device, further comprising:

receiving, by using the processing circuitry, a plurality of signals using the electrodes, wherein the signals include the one or more subcutaneous tissue impedance signals and at least one electrocardiogram (ECG).

27. A non-transitory computer-readable storage medium having stored thereon instructions that, when executed, cause one or more processors to at least:

determine, based at least in part on one or more subcutaneous tissue impedance signals of interstitial fluid sensed via only a plurality of electrodes on a housing of an insertable cardiac monitor (ICM), a plurality of tissue impedance values, wherein at least two electrodes of the plurality of electrodes are positioned within 5 centimeters (cm) apart on the housing;

determine, based at least in part on the plurality of tissue impedance values, one or more fluid index values;

determine an adaptive threshold based on an absolute impedance value of at least one of the one or more subcutaneous tissue impedance signals;

perform a comparison of the one or more fluid index values and the adaptive threshold; and determine a health condition status based at least in part on the comparison.

* * * * *